(12) United States Patent
Dee

(10) Patent No.: US 8,753,401 B2
(45) Date of Patent: Jun. 17, 2014

(54) JOINT SUPPORT AND SUBCHONDRAL SUPPORT SYSTEM

(75) Inventor: Derek Dee, Rancho Palos Verdes, CA (US)

(73) Assignee: Subchondral Solutions, Inc., Los Gatos, CA (US)

( * ) Notice: Subject to any disclaimer, the term of this patent is extended or adjusted under 35 U.S.C. 154(b) by 0 days.

(21) Appl. No.: 13/420,825

(22) Filed: Mar. 15, 2012

(65) Prior Publication Data

US 2012/0185044 A1 Jul. 19, 2012

Related U.S. Application Data

(63) Continuation of application No. 12/328,493, filed on Dec. 4, 2008, now abandoned.

(51) Int. Cl.
*A61F 2/30* (2006.01)

(52) U.S. Cl.
USPC .................................. 623/18.11; 623/16.11

(58) Field of Classification Search
USPC .......... 623/14.12, 16.11, 17.11, 17.16, 18.11, 623/20.14
See application file for complete search history.

(56) References Cited

U.S. PATENT DOCUMENTS

| | | | |
|---|---|---|---|
| 4,055,862 A | 11/1977 | Farling |
| 4,344,193 A | 8/1982 | Kenny |
| 4,502,161 A | 3/1985 | Wall |
| 4,654,314 A | 3/1987 | Takagi et al. |
| 4,687,675 A | 8/1987 | Nakano et al. |
| 4,728,332 A | 3/1988 | Albrektsson |
| 4,880,429 A | 11/1989 | Stone |
| 4,919,667 A | 4/1990 | Richmond |
| 4,963,145 A | 10/1990 | Takagi et al. |
| 5,007,934 A | 4/1991 | Stone |
| 5,026,373 A | 6/1991 | Ray et al. |
| 5,171,322 A | 12/1992 | Kenny |
| 5,306,311 A | 4/1994 | Stone et al. |
| 5,344,459 A | 9/1994 | Swartz |
| 5,865,849 A | 2/1999 | Stone |
| 6,037,519 A | 3/2000 | McKay |
| 6,042,610 A | 3/2000 | Li et al. |
| 6,046,379 A | 4/2000 | Stone et al. |
| 6,093,204 A | 7/2000 | Stone |

(Continued)

FOREIGN PATENT DOCUMENTS

| | | |
|---|---|---|
| EP | 0739631 B1 | 3/2003 |
| EP | 1719532 A3 | 7/2011 |

(Continued)

OTHER PUBLICATIONS

Dee, Derek, Office Action dated Apr. 7, 2011 issued in related U.S. Appl. No. 12/328,493, filed Dec. 4, 2008.

(Continued)

*Primary Examiner* — Thomas J Sweet
*Assistant Examiner* — Megan Wolf
(74) *Attorney, Agent, or Firm* — Kilpatrick Townsend and Stockton LLP

(57) ABSTRACT

A joint support and subchondral support system and method of use of same for providing structural and dampening support to damaged subchondral bone adjacent to a body joint are disclosed. The joint support and subchondral support system and method of use of same are applicable to many parts of the joint as any area with cartilage disease has an adjoining subchondral component.

12 Claims, 28 Drawing Sheets

(56) References Cited

U.S. PATENT DOCUMENTS

| | | | |
|---|---|---|---|
| 6,149,651 | A | 11/2000 | Drewry et al. |
| 6,193,755 | B1 | 2/2001 | Metz-Stavenhagen et al. |
| 6,206,927 | B1 | 3/2001 | Fell et al. |
| D450,122 | S | 11/2001 | Michelson |
| 6,540,786 | B2 | 4/2003 | Chibrac et al. |
| 6,629,997 | B2 | 10/2003 | Mansmann |
| 6,645,251 | B2 | 11/2003 | Salehi et al. |
| 6,699,252 | B2 | 3/2004 | Farr, II et al. |
| 6,758,865 | B1 | 7/2004 | Stone et al. |
| 6,761,739 | B2 | 7/2004 | Shepard |
| 6,783,550 | B2 | 8/2004 | MacArthur |
| 6,793,676 | B2 | 9/2004 | Plouhar et al. |
| 6,855,165 | B2 | 2/2005 | Fell et al. |
| 6,911,044 | B2 | 6/2005 | Fell et al. |
| 6,923,831 | B2 | 8/2005 | Fell et al. |
| 6,994,730 | B2 | 2/2006 | Posner |
| 7,066,961 | B2 | 6/2006 | Michelson |
| 7,282,063 | B2 | 10/2007 | Cohen et al. |
| 7,291,169 | B2 | 11/2007 | Hodorek |
| 7,297,161 | B2 | 11/2007 | Fell |
| 7,338,524 | B2 | 3/2008 | Fell et al. |
| 7,608,105 | B2 | 10/2009 | Pavlov et al. |
| 8,480,757 | B2 | 7/2013 | Gage et al. |
| 2002/0173855 | A1 | 11/2002 | Mansmann |
| 2003/0040798 | A1 | 2/2003 | Michelson |
| 2003/0109928 | A1 | 6/2003 | Pasquet et al. |
| 2004/0006393 | A1 | 1/2004 | Burkinshaw |
| 2004/0133275 | A1 | 7/2004 | Mansmann |
| 2004/0199250 | A1 | 10/2004 | Fell |
| 2004/0243250 | A1 | 12/2004 | Stone et al. |
| 2005/0004572 | A1* | 1/2005 | Biedermann et al. ........... 606/61 |
| 2005/0033424 | A1 | 2/2005 | Fell |
| 2005/0043813 | A1 | 2/2005 | Kusanagi et al. |
| 2005/0055101 | A1 | 3/2005 | Sifneos |
| 2005/0060037 | A1 | 3/2005 | Michelson |
| 2005/0171604 | A1 | 8/2005 | Michalow |
| 2005/0209703 | A1 | 9/2005 | Fell |
| 2005/0221703 | A1 | 10/2005 | Stone |
| 2005/0234549 | A1 | 10/2005 | Kladakis et al. |
| 2005/0267584 | A1 | 12/2005 | Burdulis, Jr. et al. |
| 2005/0278025 | A1 | 12/2005 | Ku et al. |
| 2006/0173542 | A1 | 8/2006 | Shikinami |
| 2006/0190078 | A1 | 8/2006 | Fell |
| 2006/0224244 | A1 | 10/2006 | Thomas et al. |
| 2007/0005143 | A1 | 1/2007 | Ek et al. |
| 2007/0179610 | A1 | 8/2007 | Biedermann et al. |
| 2008/0077248 | A1 | 3/2008 | Murillo et al. |
| 2009/0024229 | A1 | 1/2009 | Chen et al. |
| 2010/0145451 | A1 | 6/2010 | Dee |
| 2011/0029081 | A1 | 2/2011 | Malone |
| 2011/0125264 | A1 | 5/2011 | Bagga et al. |
| 2012/0172880 | A1 | 7/2012 | Dee |
| 2013/0035764 | A1 | 2/2013 | Sharkey et al. |

FOREIGN PATENT DOCUMENTS

| | | |
|---|---|---|
| EP | 2174674 B1 | 1/2012 |
| EP | 2308027 B1 | 4/2013 |
| RU | 2146503 C1 | 3/2000 |
| RU | 2161929 C1 | 1/2001 |
| WO | 98/41246 A2 | 9/1998 |
| WO | 03/007879 A2 | 1/2003 |
| WO | 2010/065426 A2 | 6/2010 |
| WO | 2013/137889 A1 | 9/2013 |

OTHER PUBLICATIONS

Dee, Derek, Office Action dated Sep. 16, 2011 issued in related U.S. Appl. No. 12/328,493, filed Dec. 4, 2008.

Dee, Derek, Office Action dated Nov. 30, 2011 issued in related U.S. Appl. No. 12/328,493, filed Dec. 4, 2008.

Dee, Derek, PCT Patent Application No. PCT/US2012/029291 filed Mar. 15, 2012.

International Search Report and Written Opinion of Application No. PCT/US2012/029291, Jul. 13, 2012, 10 pages.

International Search Report and Written Opinion of Application No. PCT/US2009/065993, Aug. 13, 2010, 15 pages.

* cited by examiner

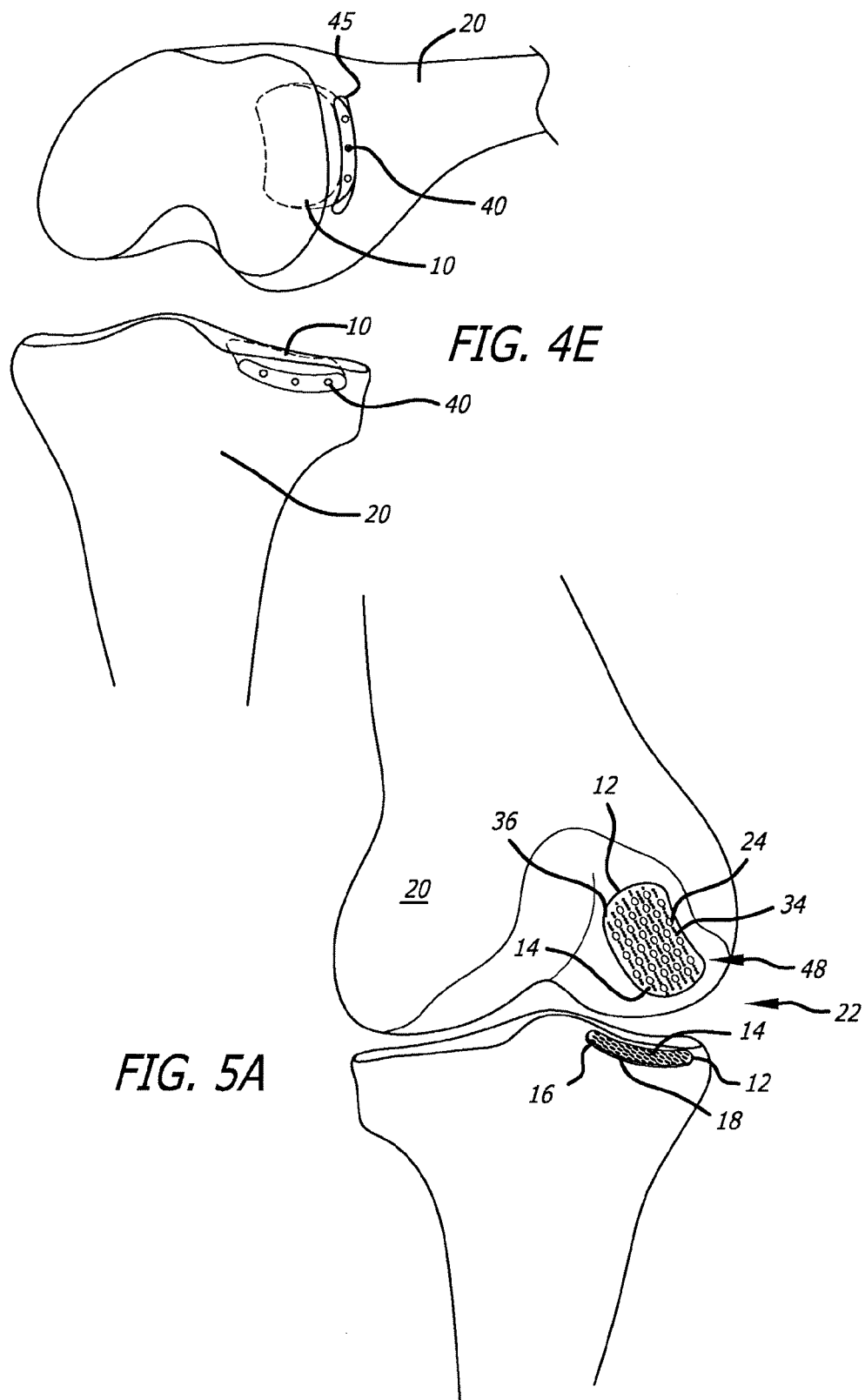

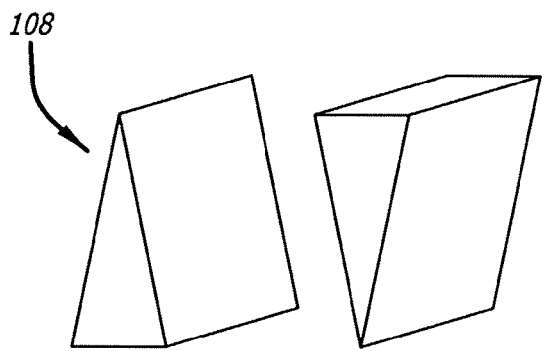
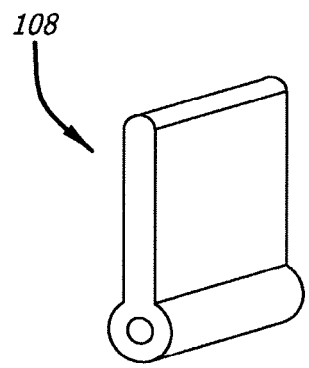
FIG. 17A      FIG. 17B
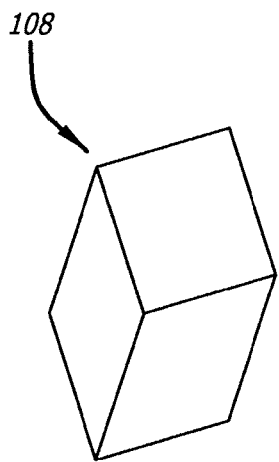
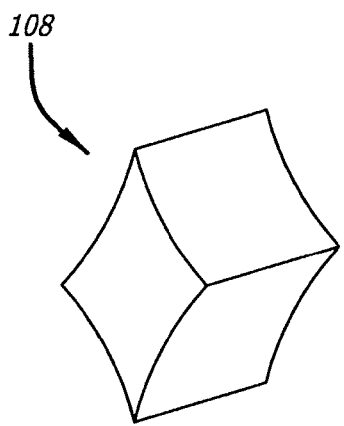
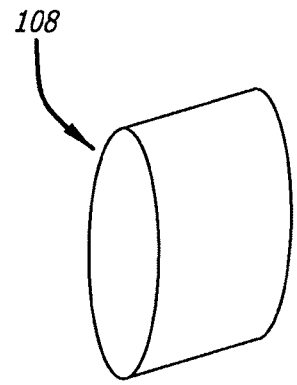
FIG. 17C      FIG. 17D      FIG. 17E
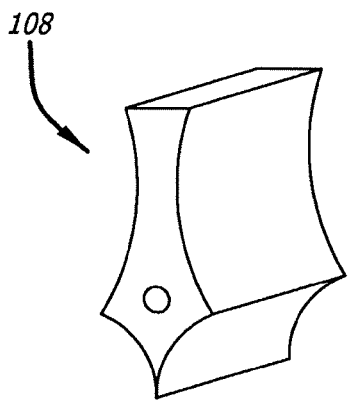
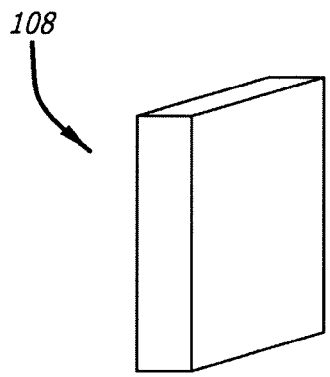
FIG. 17F      FIG. 17G

JOINT SUPPORT AND SUBCHONDRAL SUPPORT SYSTEM

CROSS-REFERENCE TO RELATED APPLICATIONS

This is a continuation application of U.S. patent application Ser. No. 12/328,493, filed Dec. 4, 2008, which is incorporated herein by reference in its entirety.

FIELD OF THE INVENTION

The present invention relates to the field of medical devices, and more specifically to a joint support and subchondral support system and method of use of same for providing structural and dampening support in the treatment of damaged subchondral bone in the disease process of joints such as osteoarthritis, chondral defects, and osteonecrosis, in humans or animals.

BACKGROUND OF THE INVENTION

Isolated articular cartilage defects and generalized cartilage disease, athroses and arthritis, respectively, in human and animal joints have certain surgical treatment options, which attempt to mimic or recreate normal anatomy and joint mechanics and/or relieve symptoms of discomfort, instability, or pain. Isolated disease often progresses to generalized disease, or arthritis—the process is a continuum. Generalized arthritis may also develop without known prior isolated disease. Arthritis may be present as a uni-, bi-, or tri-compartmental disease.

Uni-compartmental arthritis is typically less amenable to surgical options used for smaller isolated articular defects. With advanced cartilage degeneration and joint space narrowing, there is typically increased axial deformity and misalignment. Surgical options include osteotomy or uni-compartmental replacement. Options for bi- or tri-compartmental arthritis are combined procedures or total knee replacement.

Cartilage disease has been previously addressed by various means of replacing or substituting the damaged cartilage. Microfracture or abrasionplasty is a form of irritating exposed bone to create replacement fibrocartilage, but the resultant material is inferior to native cartilage. Osteochondral transplant replaces plugs of diseased cartilage and accompanying subchondral bone with grafts from either the patient or human cadaver. Small discrete lesions work well, but larger lesions, bipolar disease, and diffuse disease are not well addressed. Chondrocyte implantation harvests the patient's cartilage cells, grows them, and re-implants them on the bony bed, and covers them with a periosteal patch. Each of the aforementioned techniques work best for small contained lesions, unipolar defects (i.e., one side of joint), and primarily femoral condyle lesions. Less optimal results occur with patellofemoral joint disease, and tibial sided disease.

A further method of treating cartilage disease is to realign the joint with an osteotomy. This relieves an overloaded compartment, transferring stress to a less diseased compartment. Success of this method involves avoiding non-union and other complications, and requires prolonged non-weight bearing activity and eight to twelve months to realize clinical benefits. Only patients with mostly uni-compartmental disease are candidates. Osteotomy also complicates latter joint replacement.

Arthroscopy is used to treat other causes of pain from arthritis, namely, loose bodies, loose or frayed cartilage, meniscus tears, and synovitis. These are temporizing measures.

The end stage of cartilage disease is to perform total joint reconstruction. This type of procedure presents a prolonged recovery time and surgical risks. Because total joint prostheses are fabricated of metal and plastic, revision surgery for worn-out components is fraught with much higher complications than primary surgery, and is inevitable if the patient lives much beyond ten years.

Not much is known about the cause and progression of arthritis. With current diagnostic techniques such as MRI and bone scintigraphy, more has been elucidated about the disease process. In particular, the subchondral bone plays an important role in the initiation and progression of arthritis. Arthritis is a disease of not just the cartilage, but the underlying subchondral bone as well. Most of the clinical research to date is focused on cartilage regeneration/replacement and not on the underlying bone health.

Traditionally, cartilage has been viewed to be avascular, with diffusion of nutrients occurring from within the joint. Studies have confirmed, however, that subchondral bone is a source of vascular and nutritional support for cartilage. With age, vascular and structural support from the subchondral bone diminishes, allowing arthritic disease to progress. Namely, the inability of the bone to adequately repair itself as increasing damage occurs starts a cycle of further destruction, interfering with cartilage vascular supply and structural support.

As cartilage wear occurs, the primary functions of cartilage—to provide a low-friction bearing surface and to transmit stresses to the underlying bone—are diminished. Bone is most healthy when resisting compressive stresses. The shear stresses from the joint are partially converted to compression and tension via the architecture of the cartilage baseplate, the layer between the cartilage and underlying bone is undulating. Further, by virtue of the ultra low friction surface of cartilage on cartilage (20× lower friction than ice on ice), shear stresses are mostly converted to longitudinal. The subchondral bone is the predominant shock absorber of joint stress. Via its arch-like lattice-work of trabecular bone, stresses are transmitted to the outer cortices and ultimately dissipated. Cartilage itself does very little shock absorption secondary to its shear thickness and mechanical properties.

Bone is the ultimate shock absorber, with fracture being the endpoint of force attenuation. Trabecular microfractures have been shown to occur in locations of bone stress in impulsively loaded joints. Every joint has a physiologic envelope of function—when this envelope of function is exceeded, the rate of damage exceeds the rate of repair. As cartilage disease progresses, subchondral bone is less able to dissipate the stress it encounters, i.e., shear-type stresses. The attempts of subchondral bone to heal and remodel are seen as arthritis progresses—osteophyte formation, subchondral sclerosis, cyst formation, and subchondral MRI-enhanced changes, and increased signal on bone scintigraphy. Joint deformity from these changes further increases joint reaction force. Cartilage homeostasis is compromised—structural, vascular, neural, and nutritional.

Clinical success of current cartilage surgery is limited as it generally only works for small, uni-polar (one-sided joint) lesions of the femoral condyle. No current treatment exists for bone edema or osteonecrosis of the knee.

It would be desirable to have a minimally invasive joint support and subchondral support system and method of use of same that specifically addresses the subchondral bone in arthritic disease process and progression, and relieves the pain that results from diseased subchondral bone and the spectrum of symptoms that result from arthritis, including pain, stiffness, swelling, and discomfort. It would be further desirable to have a joint support and subchondral support system and method of use of same that provides as follows: (1) a treatment specifically for bone edema and bone bruises and osteonecrosis that has previously not existed; (2) structural scaffolding to assist in the reparative processes of diseased bone next to joints; (3) shock absorbing enhancement to subchondral bone; (4) compressive, tensile, and especially shear stress attenuation enhancement to subchondral bone; (5) a means to prevent further joint deformity from subchondral bone remodeling such as osteophyte formation; (6) assistance in the healing of or prevention of further destruction of overlying cartilage by maintaining and allowing vascularity and nutritional support from subchondral bone; (7) assistance in the healing of or prevention of further destruction of overlying cartilage by providing an adequate structural base; (8) a minimally invasive alternative to total joint reconstruction that also does not preclude or further complicate joint reconstruction; (9) a treatment for subchondral bone disease in its role in arthritis and delay or halt further progression; (10) an implant for arthritis that is minimally subject to loosening or wear, as it is integral to the trabecular framework it supports; (11) an alternative for tibial sided, patellofemoral, and bipolar disease (tibial-femoral) that is relatively easy to perform, as an adjunct to arthroscopy, and as an outpatient procedure with minimal downtime for the patient; (12) a treatment for arthritis that allows higher lever of activity than that allowed after joint resurfacing or replacement; (13) a cost effective alternative to joint replacement with less issues about the need for revision and surgical morbidity, especially in countries with less medical resources; and (14) a treatment option in veterinary medicine, specifically in equine arthroses and arthritides, among other desirable features, as described herein.

SUMMARY OF THE INVENTION

The present invention provides a joint support and subchondral support system or device and method of use of same for the treatment of damaged subchondral bone in arthritic disease process and progression. The present invention is described herein for the human knee joint, but the device and method of use of same may apply to other joints and species. In a first aspect, the present invention includes a joint support and subchondral support system for providing structural and dampening support to damaged subchondral bone adjacent to a body joint. The joint support and subchondral support system includes at least one non-telescoping single walled primary bearing strut element of variable geometry and thickness having a longitudinal body with open opposing ends and a vertically disposed inner edge and a vertically disposed outer edge, suitable for insertion within the subchondral bone. The longitudinal body has a porosity to allow vascularity, bridging bone, and other biological elements to pass through. The vertically disposed inner edge has pronged scalloping at a bottom end to penetrate the subchondral bone during insertion and to maintain the at least one non-telescoping primary bearing strut element in place within the subchondral bone. The vertically disposed outer edge has a plurality of hollow grooves formed vertically therethrough, wherein the plurality of hollow grooves are configured to receive a multi-pronged longitudinal insertion holder during insertion of the at least one non-telescoping primary bearing strut element within the subchondral bone, and the vertically disposed outer edge is contoured to fit the subchondral bone at a treatment site.

In certain embodiments, the multi-pronged longitudinal insertion holder forms a plurality of vascular channels in the subchondral bone during insertion of the at least one non-telescoping primary bearing strut element within the subchondral bone whereby blood or marrow may access the vertically disposed outer edge through the plurality of hollow grooves or vascular channels.

In certain embodiments, single or multiple geometric shapes of the at least one non-telescoping primary bearing strut element may be configured to be joined to each other in various patterns such that the single or multiple geometric shapes penetrate the subchondral bone at the treatment site.

In certain embodiments, the single or multiple geometric shapes configured to be joined together include at least three connecting struts to form a multiple concentric circle in which each circle of the at least one non-telescoping primary bearing strut element is connected to an adjacent circle by the connecting struts.

In certain embodiments, the at least one non-telescoping primary bearing strut element has a diameter of from about 1 mm to about 5 cm and a height/depth of from about 1 mm to about 3 cm.

In certain embodiments, the at least one non-telescoping primary bearing strut element includes a primary bearing flare for resisting subsidence within the subchondral bone at the treatment site.

In certain embodiments, the at least one non-telescoping primary bearing strut element includes a secondary flare extending below the strut element for further resisting subsidence within the subchondral bone at the treatment site.

In certain embodiments, the secondary flare is at least one of a vertical, double-tapered wing strut, and obliquely extending arm.

In certain embodiments, the porosity of the longitudinal body may be comprised of micropores, scaffold-like pores, or a fibrous matrix material.

In certain embodiments, the at least one non-telescoping primary bearing strut element includes a concentric taper from the vertically disposed outer edge to the inner edge.

In certain embodiments, the at least one non-telescoping primary bearing strut element may have a geometry in the form of a multiple concentric circle, joined circles, hexagon, octagon, or other non-euclidean shapes.

In certain embodiments, a biocompatible bearing surface cover may be attached to a periphery of the vertically disposed outer edge to contain marrow contents entering through vascular channels or exogenous substances injected through the cover.

In certain embodiments, at least one active or passive dampening element is attached to the at least one non-telescoping primary bearing strut element for dissipating and dampening shock within the subchondral bone.

In a further aspect, there is provided herein a method of providing structural and dampening support to damaged subchondral bone adjacent to a body joint. The method includes providing at least one non-telescoping primary bearing strut element of variable geometry and thickness having a longitudinal body and a vertically disposed inner edge and outer edge, suitable for insertion within the subchondral bone. The vertically disposed outer edge is contoured to fit the subchondral bone at the treatment site. The method further includes providing a multi-pronged longitudinal insertion holder and configuring the vertically disposed outer edge to have a plurality of hollow grooves formed vertically therethrough for receiving the multi-pronged longitudinal insertion holder. The subchondral bone is penetrated during insertion of the at least one non-telescoping primary bearing strut element within the subchondral bone at the treatment site. The at least one non-telescoping primary bearing strut element is maintained in place within the subchondral bone. Vascularity, bridging bone, and other biological elements, are allowed to pass through a porosity of the longitudinal body when positioned at the treatment site.

In certain embodiments, the step of configuring the vertically disposed outer edge to have a plurality of hollow grooves formed vertically therethrough includes slidably disposing the multi-pronged longitudinal insertion holder downward through the plurality of hollow grooves at the vertically disposed outer edge during insertion of the at least one non-telescoping primary bearing strut element within the subchondral bone at the treatment site.

In certain embodiments, the step of penetrating the subchondral bone includes forming a plurality of vascular channels in the subchondral bone during insertion of the at least one non-telescoping primary bearing strut element within the subchondral bone whereby blood or marrow may access the vertically disposed outer edge through the plurality of hollow grooves or vascular channels.

In certain embodiments, the step of penetrating the subchondral bone includes configuring the vertically disposed inner edge and outer edge to have pronged scalloping at a bottom end suitable for penetrating the subchondral bone during insertion of the at least one non-telescoping primary bearing strut element within the subchondral bone at the treatment site.

In certain embodiments, the step of penetrating the subchondral bone includes tamping the at least one non-telescoping primary bearing strut element and multi-pronged longitudinal insertion holder into the subchondral bone and removing the multi-pronged longitudinal insertion holder from the treatment site.

In certain embodiments, the step of maintaining the at least one non-telescoping primary bearing strut element in place within the subchondral bone includes configuring the vertically disposed inner edge and outer edge to have pronged scalloping at a bottom end thereof.

In certain embodiments, the step of maintaining the at least one non-telescoping primary bearing strut element in place within the subchondral bone includes configuring the at least one non-telescoping primary bearing strut element to have a primary bearing flare for resisting subsidence within the subchondral bone at the treatment site.

In certain embodiments, the step of maintaining the at least one non-telescoping primary bearing strut element in place within the subchondral bone includes configuring the at least one non-telescoping primary bearing strut element to have a secondary flare extending below the strut element for further resisting subsidence within the subchondral bone at the treatment site.

In certain embodiments, the step of configuring the at least one non-telescoping primary bearing strut element to have a secondary flare extending below the strut element includes forming the secondary flare as a vertical, double-tapered wing strut or an obliquely extending arm.

In certain embodiments, the step of allowing vascularity, bridging bone, and other biological elements to pass through a porosity of the longitudinal body includes configuring the porosity of the longitudinal body to be comprised of micropores, scaffold-like pores, or a fibrous matrix material.

These and other features and advantages of this invention will become further apparent from the detailed description and accompanying figures that follow. In the figures and description, numerals indicate the various features of the disclosure, like numerals referring to like features throughout both the drawings and the description.

BRIEF DESCRIPTION OF THE DRAWINGS

FIGS. 4A-4E illustrate the placement of the device of FIG. 1 in subchondral bone of the tibial plateau.

FIG. 5A illustrates the placement of the device of FIG. 1 in subchondral bone of the femoral condyle and the tibial plateau as a monobloc insert.

FIGS. 17A-17G illustrate an enlarged perspective view of each of the different cross-sectional shapes of the device of FIG. 14A.

DETAILED DESCRIPTION OF THE INVENTION

Figure 1:
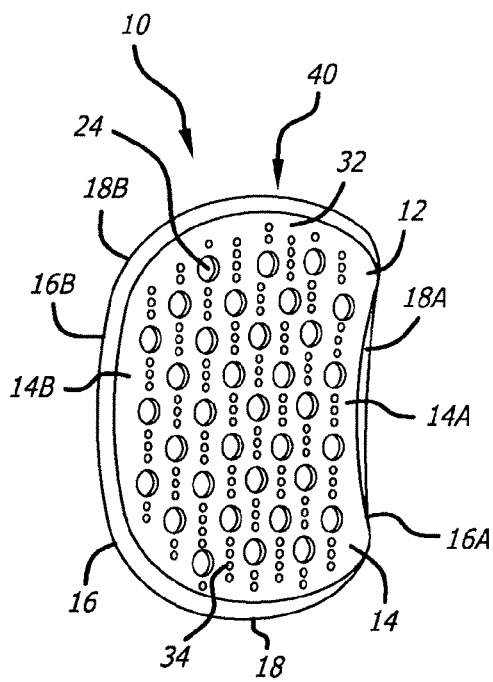
FIG. 1 is a perspective view of an embodiment of a joint support and subchondral support system according to the present invention.

The joint support and subchondral support system or device 10 of the present invention is generally illustrated in FIG. 1. It is contemplated by the present invention that the joint support and subchondral support system is not a substitute for partial or total joint replacement, but may delay the need for joint replacement in active individuals with moderate osteoarthritis and/or arthroses. By sustaining subchondral bone homeostases, further joint deformity and disease progression may be delayed and/or avoided. The joint support and subchondral support system in accordance with the present invention enhances and reinforces the cartilage-bone complex in the presence of diseased cartilage or a cartilage defect. It treats the bony side of the equation by mechanical absorption of shear and compressive stresses that threaten cartilage-bone homeostasis.

A number of advantages of the joint support and subchondral support system in accordance with the present invention are evident as follows: (1) the basic structure and mechanics of the system are applicable to many parts of the joint, as any area with cartilage disease has an adjoining subchondral component; (2) minimal modifications in manufacturing are necessary to apply this system to multiple areas, namely, the contour of the porous, plate closest to the joint; (3) the device may be inserted with minimal soft tissue dissection and minimal to no violation of the joint capsule if done in retrograde or side-slot insertion methods; (4) antegrade devices also may be inserted with a minimal arthrotomy; for diffuse lesions with long anterior-posterior dimensions, two devices may be placed anterior and posterior to each other through the same small arthrotomy; (5) the system is inherently stable, as it occupies little space within the bone and is a joint scaffolding, not a replacement; and (6) the materials that comprise the system are dampening, thereby enhancing the trabecular bone's ability to withstand shock and shear stress.

The joint support and subchondral support system 10 includes a contoured, porous plate 12 having a variable shaped inner surface 14, outer surface 16, and peripheral surface 18 of variable thickness extending between the inner surface 14 and the outer surface 16, suitable for insertion within the subchondral bone 20. The contoured, porous plate 12 inner surface 14, outer surface 16, and peripheral surface 18 may be kidney-shaped, oval-shaped, or otherwise so shaped to fit within the subchondral bone 20 at the desired anatomic site. The inner surface 14, outer surface 16, and peripheral surface 18 each have a respective concave portion 14A, 16A, 18A, and a respective convex portion 14B, 16B, 18B. The inner surface 14 of the contoured, porous plate 12 is closest to the joint 22 and the first part of the system 10 that encounters stress. The inner surface 14 is configured to fit flush with the respective geometries of the tibial and femoral sides of the joint 22, and may be convex, concave, or complex to minor the particular anatomic location. The outer surface 16 will mirror the geometry of the inner surface 14. The geometry of the inner surface 14, outer surface 16, and peripheral surface 18, may vary depending on the exact anatomic location being treated (i.e., proximal tibia versus femoral trochlea) and the specific geometry of the lesion being treated.

The contours 32 of the porous plate 12 may be configured to match the chondral/subchondral curvature and anatomy of the specific joint 22 location. Alternatively, the contours 32 may not be configured to match the chondral/subchondral 20 curvature and anatomy of the specific joint 22 location such that the contours 32 are neutral or assume a reverse or varied polarity.

Figure 2A:
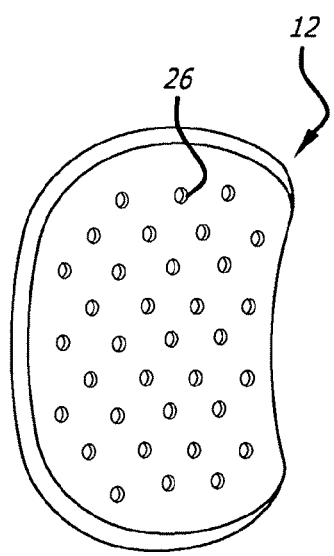
FIGS. 2A-2C illustrate the various degrees of porosity of the contoured, porous plate of the embodiment of FIG. 1.
Figure 2B:
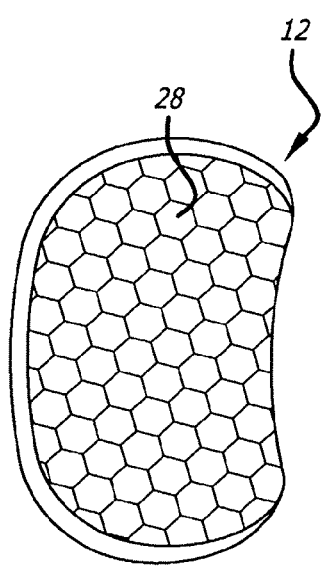
Figure 2C:
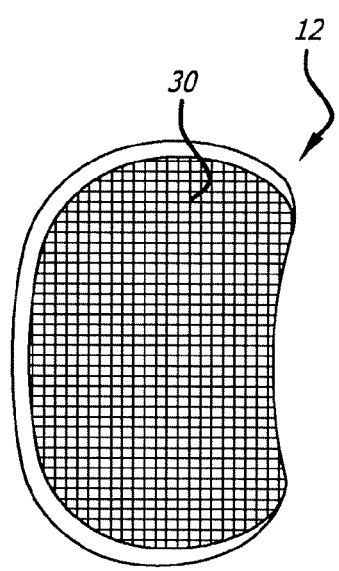

The contoured, porous plate 12 has a porosity 24 to allow vascularity and other biologic elements from the host to pass through the contoured, porous plate 12. The porosity 24 of the contoured, porous plate 12 is within a range of from about 50 microns to about 20 mm. As shown in FIGS. 2A-2C, the porosity 24 of the contoured, porous plate 12 may be comprised of micropores 26, scaffold-like pores 28, or fibrous matrix material 30.

Referring further to FIG. 1, the contoured, porous plate 12 includes a plurality of surface dimpling 34, which increases the surface area for stress absorption and converts as much shear stress to compressive or tensile stress, as the cartilage baseplate of the joint 22 has similar features. The surface dimpling 34 has a radius of from about 50 microns to about 3 mm. The contoured, porous plate 12 may further include a plurality of undersurface pimples 36, which increase the surface area below the contoured, porous plate 12 to spread the load. The undersurface pimples 36 have a radius of from about 50 microns to about 3 mm.

Figure 3A:
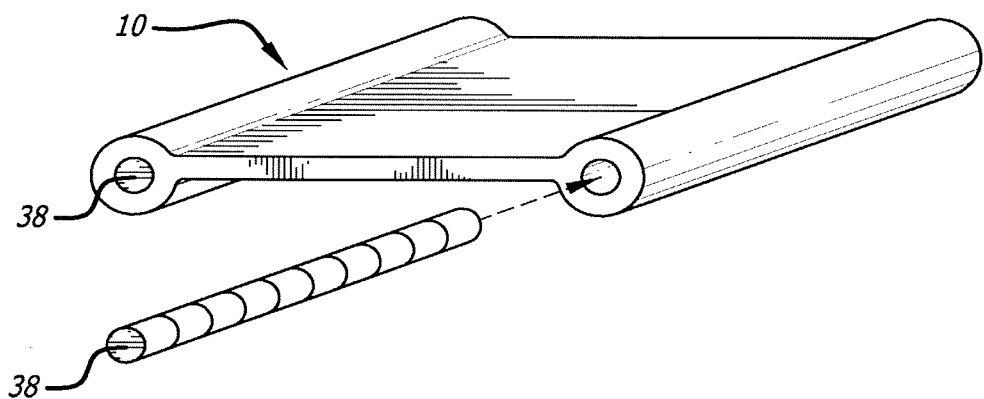
FIGS. 3A-3B are perspective views of the dampening element of the joint support and subchondral support system according to the present invention.
Figure 3B:
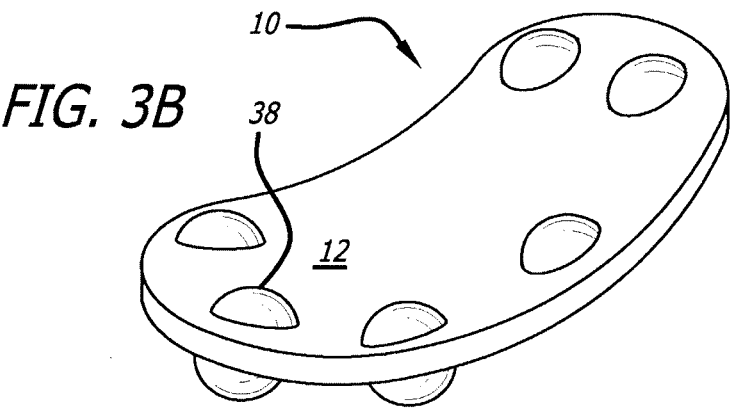
Figure 4A:
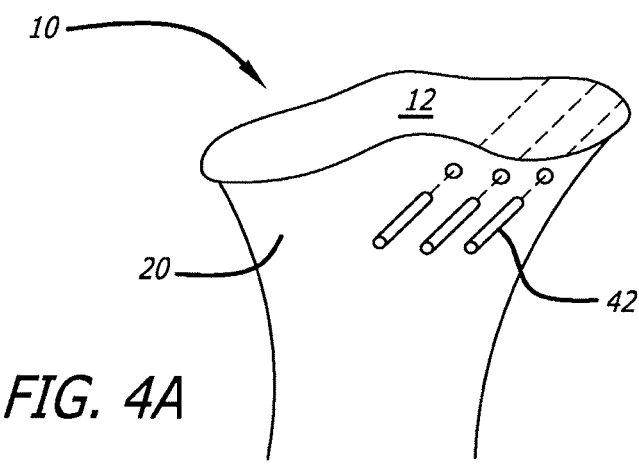
Figure 4B:
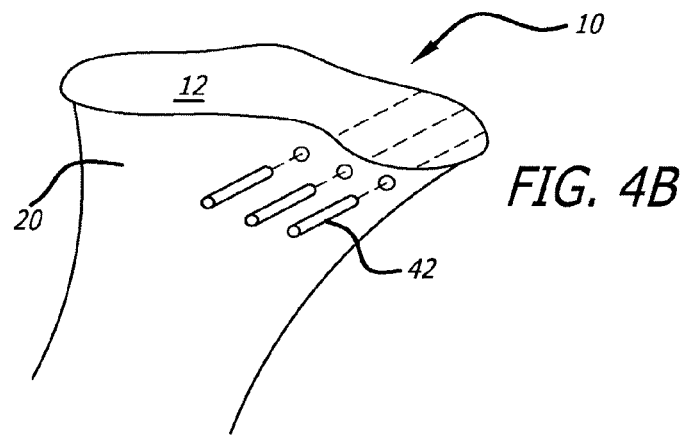
Figure 4C:
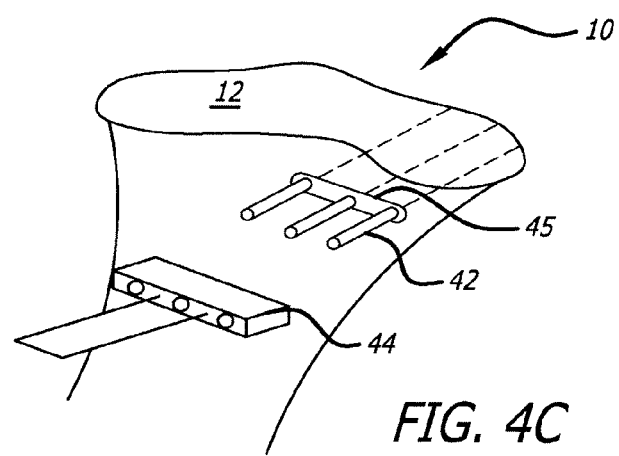
Figure 4D:
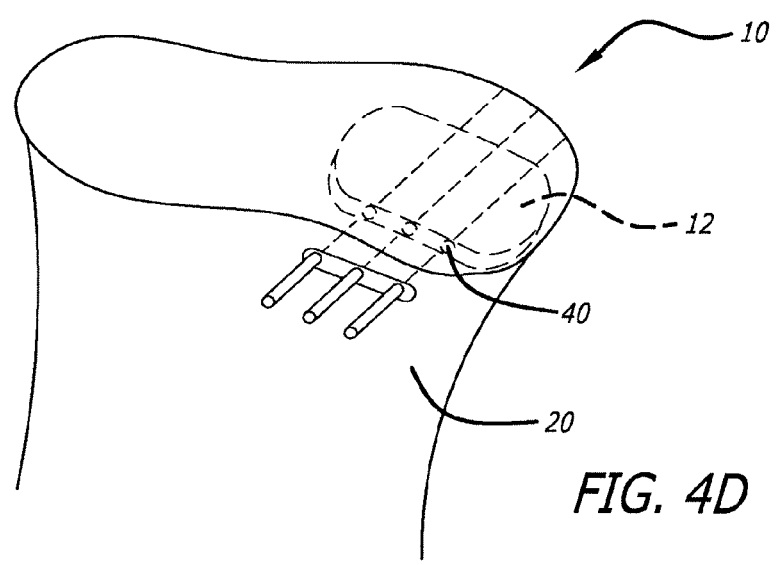

The dimensions of the system or device 10 generally depend on the size of the lesion being treated. Typically, two or more devices 10 will be deployed per location for diffuse disease and one device for smaller lesions. The vertical dimension ranges from about 1 mm to about 100 mm and the horizontal dimension ranges from about 1 mm to about 100 mm. The contoured, porous plate 12 has a cross-sectional area of from about 1 mm² to about 100 cm². The peripheral surface 18 of the contoured, porous plate 12 has a variable thickness of from about 0.1 mm to about 5 cm. At least one active or passive dampening element 38 is attached to the contoured, porous plate 12. A dampening element, such as a piezoelectric device, converts active mechanical energy to heat or electric, thereby dissipating and dampening the shock. A passive dampening element 38 may be made of silicone or other shock-absorbing material. Either active or passive dampening element 38 may be incorporated into plate as illustrated in FIGS. 3A-3B. FIG. 3A illustrates the dampening element 38 as a long cylinder housed in the periphery of the device 10. FIG. 3B illustrates the dampening element 38 as individual spheres embedded in the periphery of device 10. The dampening element 38 may also be inherent within the material properties of the device, and not a separate component, i.e., silicone-impregnated porous metal matrix.

Referring to FIG. 4, at least one to multiple guide pin holes or slots 40 are located within device 10 to aid insertion within the subchondral bone 20. The guide pin(s) 42 are inserted into the anatomic site initially (FIG. 4A) with device 10 inserted over the guide pin(s) 42 (FIG. 4B). A bone cutter/dilator 44 is inserted over the guide pin(s) 42 to create an entry opening and slot 45 for device 10 (FIG. 4C). The bone cutter or dilator 44 is smaller in dimension than device 10, thereby allowing a press-fit fixation. The device 10 is inserted over the guide pin(s) 42 via the holes or slots 40 (FIG. 4D). The excess guide pin(s) 42 may break away or be removed after device 10 is inserted within the subchondral bone 20. One guide pin 42 may be used initially as device 10 is allowed small amounts of swiveling to more exactly fit the contours of the subchondral baseplate 20. Placement of the guide pin 42 into the subchondral defect 20 may be accomplished by either fluoroscopic guidance, CT guidance, computer navigation guidance, or direct guidance. In one embodiment, the guide pin 42 may be configured to break away from the contoured, porous plate 12 upon insertion of the device 10 within the subchondral bone 20.

The operation of the device 10 for the femur involves placing a guide pin 42 into the center of the subchondral defect 20 from within the joint 22. This is followed by a bone cutter or dilator 44 to prepare the bone. The device 10 is then inserted over the guide pin 42 and positioned flush with the subchondral bone 20 with a tamp. The insertion of the device 10 is peripheral or tangential to the joint surface (FIG. 4E).

Figure 5B:
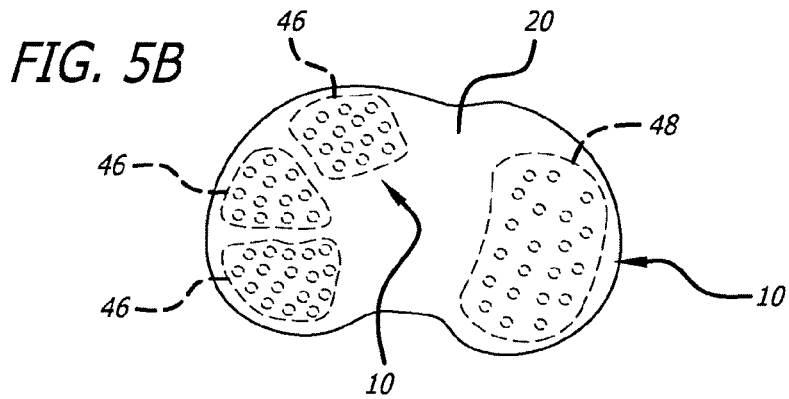
FIG. 5B is a top plan view of the placement of the device of FIG. 1 in subchondral bone of the tibial plateau as both a modular insert and a monobloc insert.
Figure 5C:
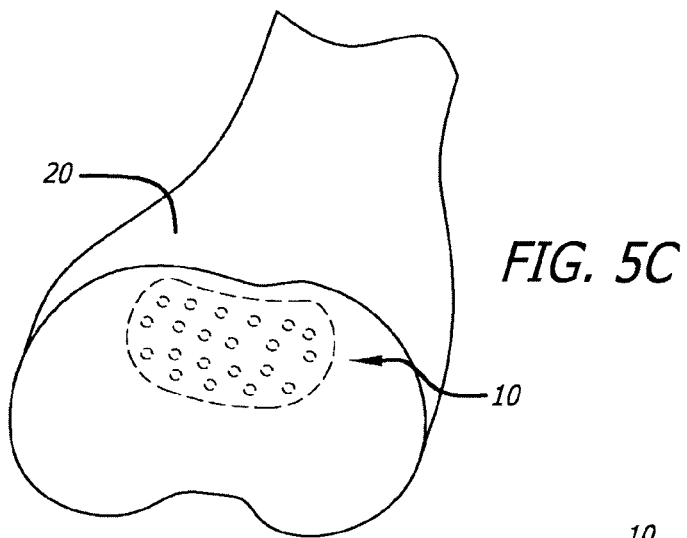
FIG. 5C is a front perspective view of the placement of the device of FIG. 1 in subchondral bone of the femoral trochlea.
Figure 5D:
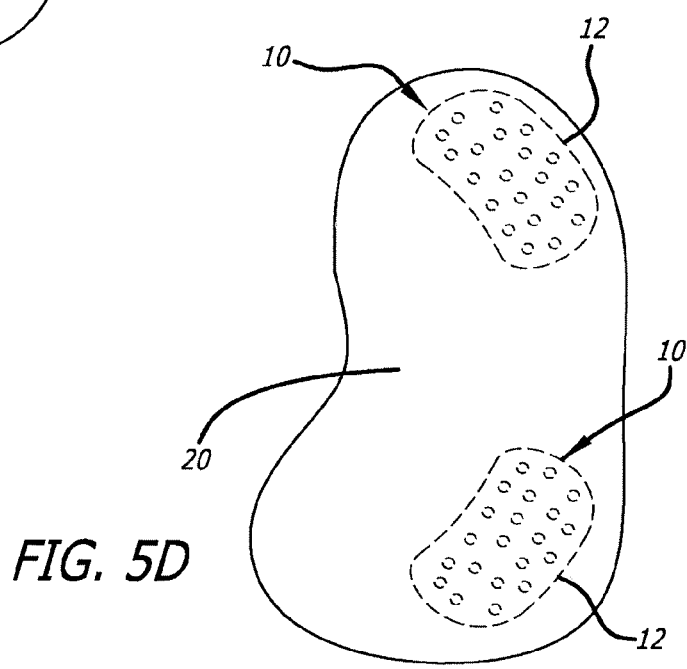
FIG. 5D is a front perspective view of the placement of the device of FIG. 1 in subchondral bone of the patella.

FIG. 5A illustrates the placement of the joint support and subchondral support system or device 10 in subchondral bone 20 of the femoral condyle and the tibial plateau as a monobloc 48 insert. FIG. 5B is a top plan view of the placement of the device 10 in subchondral bone 20 of the tibial plateau as both a modular 46 and a monobloc 48 insert. As shown in FIG. 5B, the contoured, porous plate 12 may be inserted in at least two different locations of the subchondral bone 20 as a modular 46 or monobloc 48 insert. FIG. 5C is a front perspective view of the placement of the device 10 in subchondral bone 20 of the femoral trochlea. FIG. 5D is a front perspective view of the placement of the device 10 in subchondral bone 20 of the patella.

The joint support and subchondral support system 10 of the present invention may be fabricated from virtually any biocompatible material, including, but not limited to, metals, metal alloys, carbon fibers, foam metals, ceramics, ceramic composites, elastomer composites, elastomer-carbon fiber composites, chambered or fluid-filled materials, metal matrices, injectable gels, injectable composites with fluid and sold matrices, bone or bone-composite or allografts, crystal or hydroxyapatite materials, plastics (i.e., PEEK), polymers, bioabsorbable composites (i.e., TCP/PLLA), or composites/combinations of the above materials. The preferred materials for the system 10 have inherent elastic or shock absorbing properties.

Figure 6:
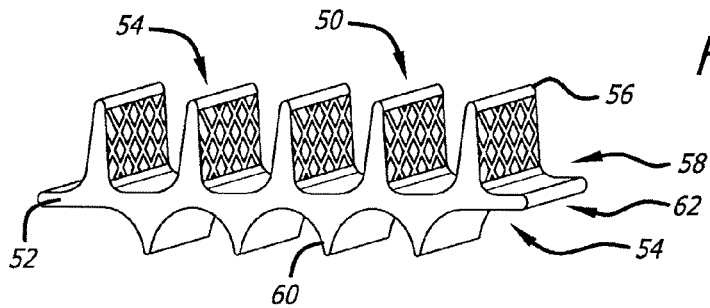
FIG. 6 is a perspective view of another embodiment of the joint support and subchondral support system according to the present invention.

In another embodiment as shown in FIG. 6, the joint support and subchondral support system or device 50 includes an elongated plate 52 having a plurality of tapered strut elements 54 of variable geometry and thickness oriented in a vertical configuration for insertion into the subchondral bone 20. The strut elements 54 include a plurality of superior struts 56 formed on an upper portion 58 of the plate 52 and a plurality of inferior struts 60 formed on a lower portion 62 of the plate 52. The plurality of inferior struts 60 may be configured to be out of plane with the plurality of superior struts 56. There may be single to multiple superior or inferior struts depending on the size of pathologic lesion being treated.

Figure 7B:
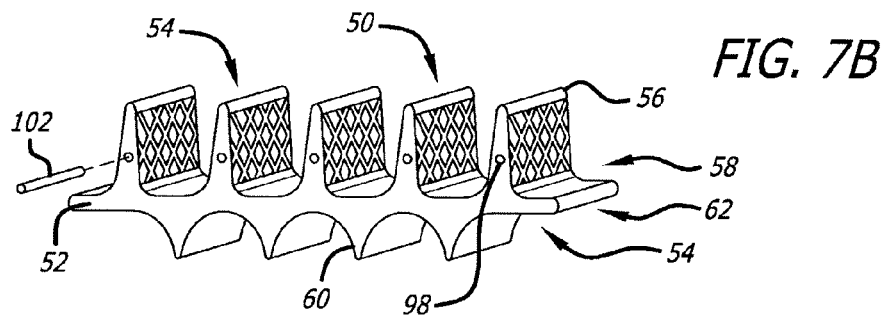
FIGS. 7A-7D illustrate the placement of the device of FIG. 6 in subchondral bone of a knee joint.
Figure 7C:
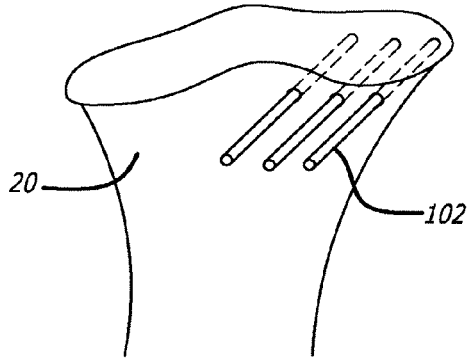
Figure 7D:
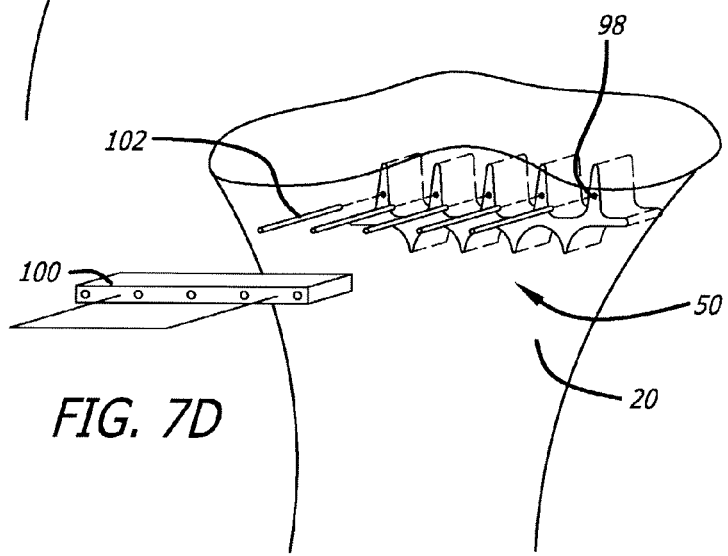
Figure 7A:
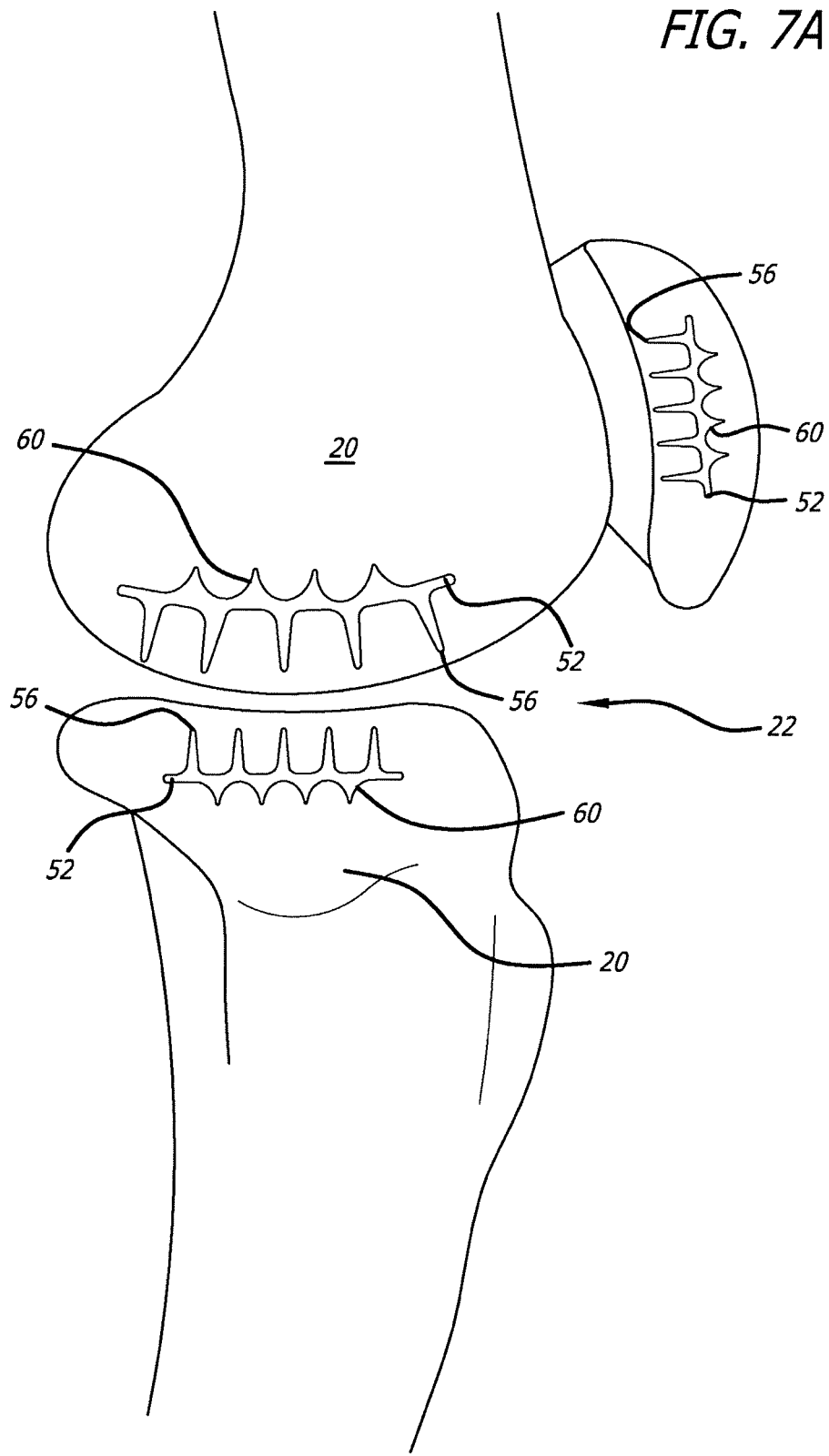

FIG. 7A illustrates the placement of the joint support and subchondral support system 50 in subchondral bone 20 of the femoral condyle and tibial plateau and patella in accordance with the present invention.

Figure 8:
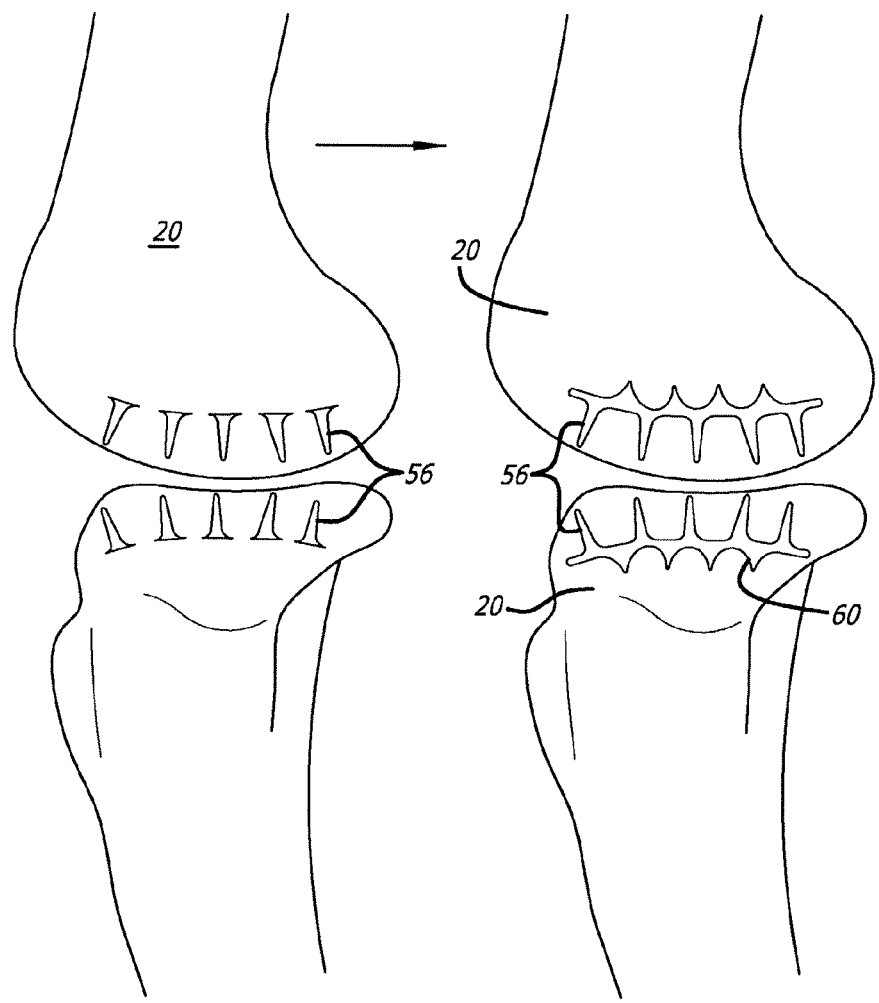
FIG. 8 illustrates the placement of the elongated plate separately from the plurality of strut elements within the subchondral bone of the knee joint as a modular insert.

It is contemplated by the present invention that the elongated plate 52 may be inserted separately from the plurality of strut elements 54 within the subchondral bone 20 as a modular insert 64 shown in FIG. 8.

The elongated plate 52 serves as a secondary bearing element and dissipates stresses centripetally and absorbs stress inherently. The elongated plate 52 thickness and material properties may vary to enable stress transmission outward. The elongated plate 52 prevents subsidence of the structural support system 50. The dimension of the elongated plate 52 is dependant on the size of lesion being treated. The vertical dimension ranges from about 1 mm to about 100 mm and the horizontal dimension ranges from about 1 mm to about 100 mm. The elongated plate 52 has a cross-sectional area of from about 1 mm² to about 100 cm².

Figure 9:
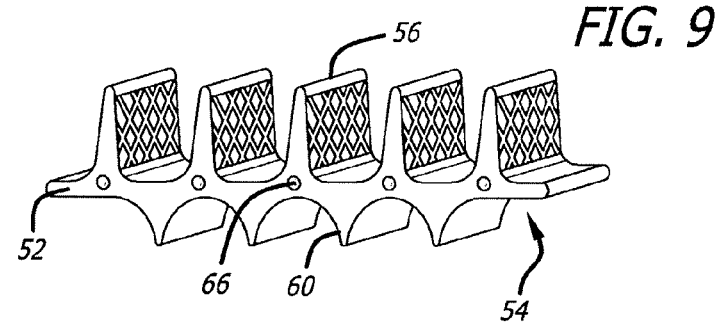
FIG. 9 is an enlarged perspective view of the elongated plate releasably attached to the plurality of strut elements of FIG. 6.

In one embodiment of FIG. 9, the elongated plate 52 is shown releasably attached to the plurality of strut elements 54 with smoothly rounded joint elements 66 at each intersection of the strut elements 54 and the elongated plate 52. The plurality of superior 56 and inferior 60 struts have a width of from about 0.1 mm to about 10 mm and a height of from about 0.5 mm to about 35 mm.

The plurality of superior struts 56 serves to accept the load from the adjoining joint 22. The level of penetration of the superior struts 56 within the subchondral bone 20 includes as follows: the superior struts 56 may stop short or come up to the cartilage base plate, may penetrate the cartilage base plate and reside in the lower cartilage layer, or may come flush to the native bearing cartilage surface. The plurality of inferior struts 60 reinforces the structural integrity of the elongated plate 52 and enables centripetal transmission/dissipation of forces to underlying and surrounding structures (i.e., bone or soft tissue).

Figure 10A:
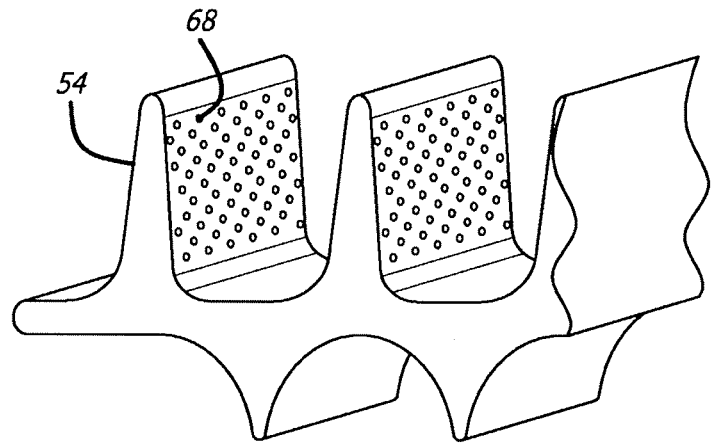
FIGS. 10A-10C illustrate the various degrees of porosity of the plurality of strut elements of the embodiment of FIG. 6.
Figure 10B:
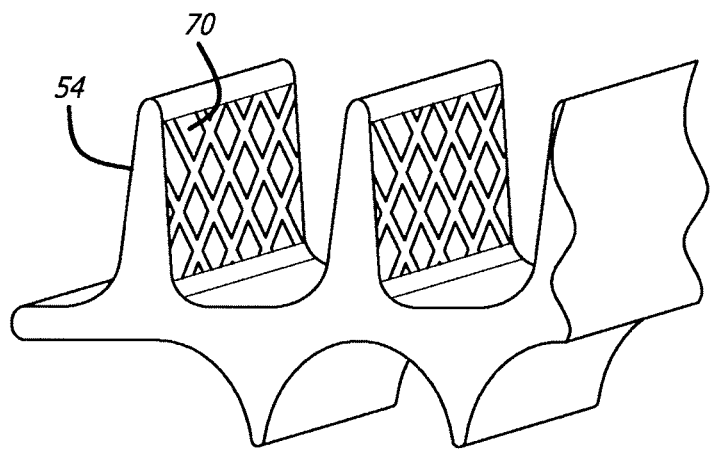
Figure 10C:
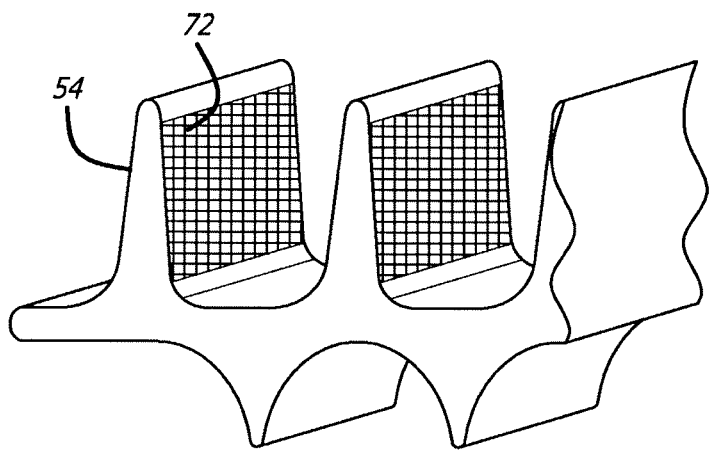

As shown in FIGS. 10A-10C, the plurality of strut elements 54 may be fabricated to have a porosity comprised of micropores 68, scaffold-like pores 70, or fibrous matrix material 72. The porosity of the plurality of strut elements is within a range of from about 50 microns to about 20 mm.

Figure 11A:
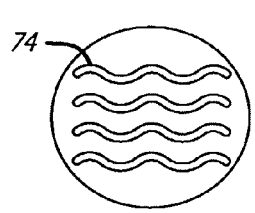
FIGS. 11A-11H illustrate a top view of several variable orientations or geometries of the plurality of strut elements of the embodiment of FIG. 6.
Figure 11B:
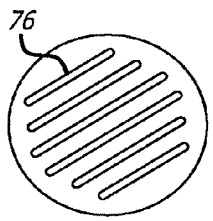
Figure 11C:
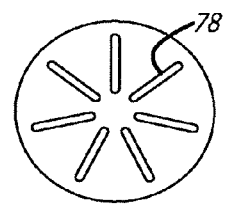
Figure 11D:
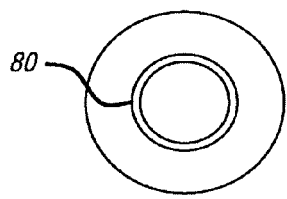
Figure 11E:
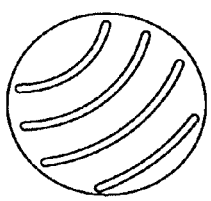
Figure 11F:
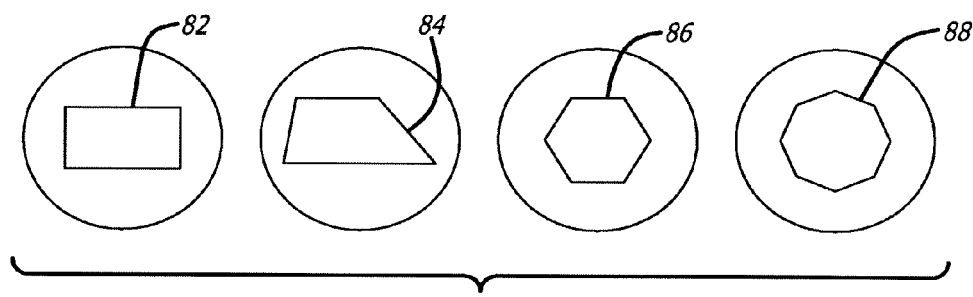
Figure 11G:
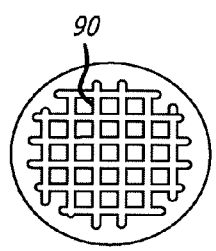
Figure 11H:
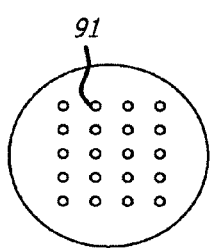

The plurality of strut elements 54 may have a variable orientation or geometry such as sinusoidal 74(FIG. 11A), parallel 76 (FIG. 11B), radial 78 (FIG. 11C), circular 80 (FIG. 11D), curved (FIG. 11E), geometric—rectangular 82, trapezoidal 84, hexagonal 86, octagonal 88 (FIG. 11F), cross-hatching or cross-elements 90 (FIG. 11G), or single columns 91 (FIG. 11H).

Figure 12A:
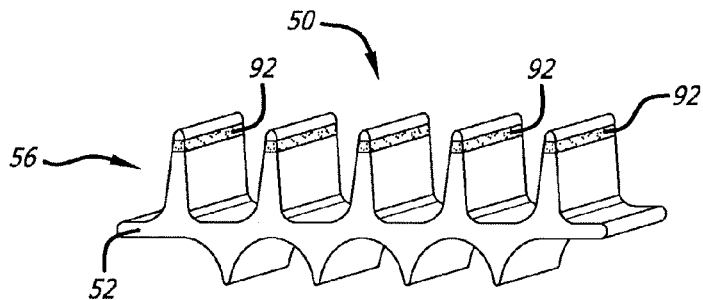
FIG. 12A illustrates an enlarged perspective view of the plurality of superior struts of the embodiment of FIG. 6.
Figure 12B:
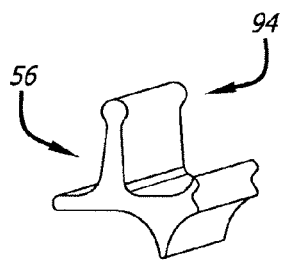
FIGS. 12B-12D illustrate various configurations of the flared bearing surface of the embodiment of FIG. 6.
Figure 12C:
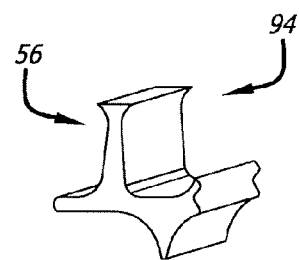
Figure 12D:
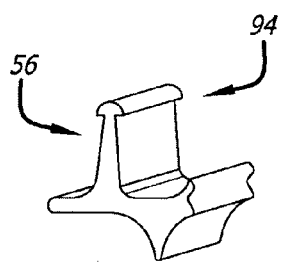
Figure 12E:
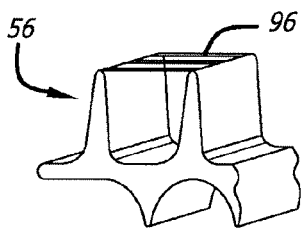
FIG. 12E is a perspective view of the secondary bearing element of the embodiment of FIG. 6.

FIG. 12A illustrates an enlarged perspective view of the plurality of superior struts 56 of the joint support and subchondral support system 50 of FIG. 6. The plurality of superior struts 56 have a primary bearing element 92 configured to be contoured such that the primary bearing element 92 is generally the same as the corresponding subchondral bone 20 being treated. The primary bearing element 92 has an ultra-low coefficient of friction surface that is polished or fabricated of a biocompatible material. The primary bearing element 92 includes a flared bearing surface 94 that is substantially wider than each of the plurality of superior struts 56. The flared bearing surface 94 may be configured to assume a variety of shapes such as circular (FIG. 12B), flat (FIG. 12C), mushroom-like (FIG. 12D), and the like. The flared bearing surface 94 has a width of from about 1.1 to about 4× a width of each of the plurality of superior struts 56. The plurality of superior struts 56 may include at least one secondary bearing element 96 (FIG. 12E) that connects the plurality of superior struts 56 to each other. The secondary bearing element 96 has a width of from about 0.5 to about 5× the width of the superior strut 56.

A guide pin hole or slot 98 is positioned within the elongated plate 52 oriented longitudinally for insertion and placement of the plate 52 and plurality of strut elements 54 over at least one corresponding guide pin 102 within the subchondral bone 20 (FIGS. 7B-7D). At least one to multiple guide pin holes or slots 98 are located within device 50 to aid insertion within the subchondral bone 20. The guide pin(s) 102 is inserted into the anatomic site initially (FIG. 7C). A bone cutter/dilator 100 is inserted over the guide pin(s) 102 to create an entry opening and slot 98 for device 50 (FIG. 7D). The bone cutter/dilator 100 is smaller in dimension than device 50, thereby allowing a press-fit fixation. The device 50 is inserted over the guide pin(s) 102 via the guide pin holes or slots 98 (FIG. 7D). The excess guide pin(s) 102 may break away or be removed after device 50 is inserted within the subchondral bone 20. Placement of the guide pin 102 into the subchondral defect 20 may be accomplished by either fluoroscopic guidance, CT guidance, computer navigation guidance, or direct guidance. In one embodiment, the guide pin 102 may be configured to break away from the elongated plate 52 upon insertion of the device 50 within the subchondral bone 20.

Referring further to FIG. 7, the operation of the device 50 for the femur involves placing a guide pin 102 into the center of the subchondral defect 20 from within the joint 22. This is followed by a bone cutter/dilator 100 to prepare the bone. The device 50 is then inserted over the guide pin 102 and positioned flush with the subchondral bone 20 with a tamp. The insertion of the device 50 is peripheral or tangential to the joint surface (FIG. 7).

Figure 13A:
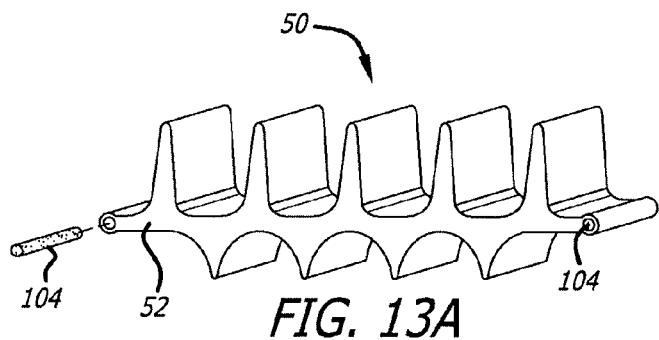
FIG. 13A is a perspective view of the dampening element as a long cylinder housed in the periphery of the device of FIG. 6.
Figure 13B:
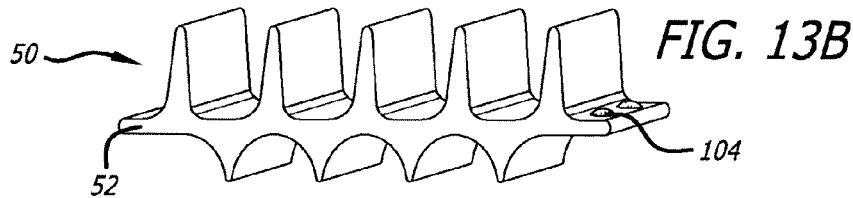
FIG. 13B is a perspective view of the dampening element as individual spheres embedded in the periphery of the device of FIG. 6.

At least one active or passive dampening element 104 is attached to the elongated plate 52 and plurality of strut elements 54 (FIG. 13). An active dampening element, such as a piezoelectric device, converts active mechanical energy to heat or electric, thereby dissipating and dampening the shock. FIG. 13A illustrates the dampening element 104 as a long cylinder housed in the periphery of the device 50. FIG. 13B illustrates the dampening element 104 as individual spheres embedded in the periphery of the device 50. A passive dampening element may be made of silicone or other shock-absorbing material. Either active or passive dampening element 104 may be incorporated into plate 52 as illustrated in FIGS. 13A-13B. The dampening element may also be inherent within the material properties of the device 50, and not a separate component, i.e., silicone-impregnated porous metal matrix.

The joint support and subchondral support system 50 of the present invention may be fabricated from virtually any biocompatible material, including, but not limited to, metals, metal alloys, carbon fibers, foam metals, ceramics, ceramic composites, elastomer composites, elastomer-carbon fiber composites, chambered or fluid-filled materials, metal matrices, injectable gels, injectable composites with fluid and sold matrices, bone or bone-composite or allografts, crystal or hydroxyapatite materials, plastics (i.e., PEEK), polymers, bioabsorbable composites (i.e., TCP/PLLA), or combinations/composites of the above materials. The preferred materials for the system 50 have inherent elastic or shock absorbing properties.

Figure 14A:
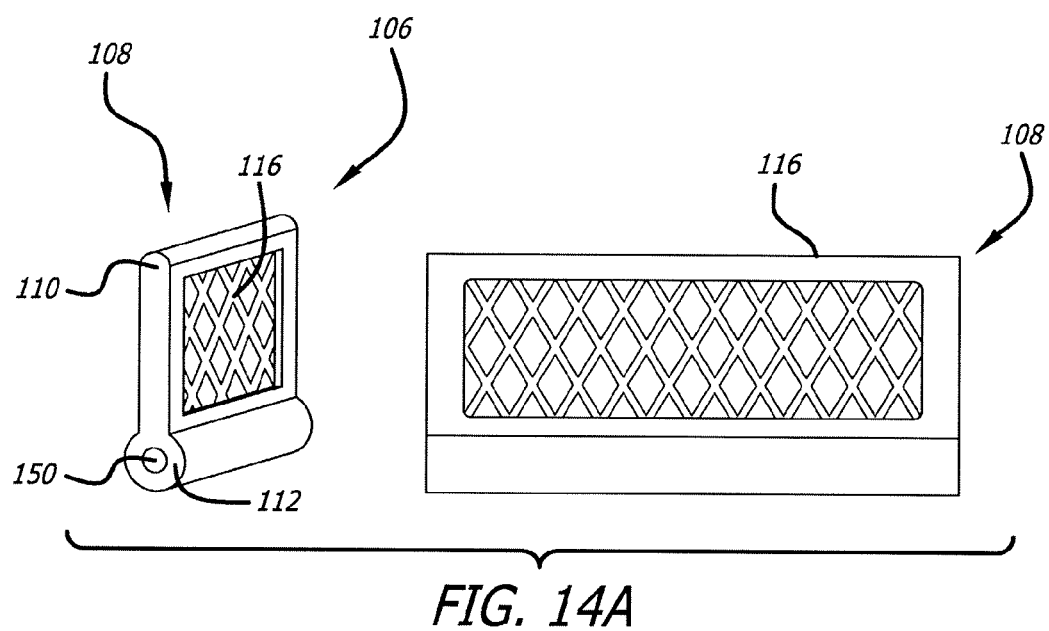
FIG. 14A is a perspective view of a further embodiment of the joint support and subchondral support system according to the present invention.
Figure 14B:
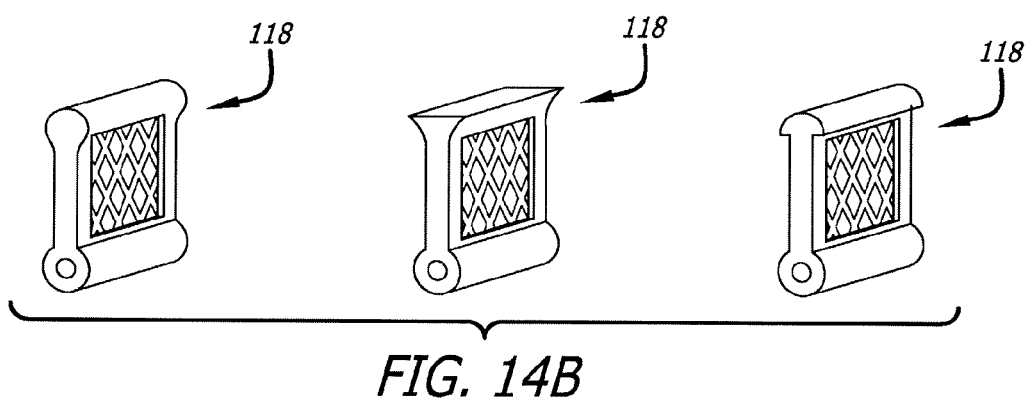
FIG. 14B illustrates the various configurations of the primary bearing flare of the device of FIG. 14A.

In a further embodiment as shown in FIG. 14A, the joint support and subchondral support system 106 includes a plurality of separate vertical struts 108 of variable geometry and thickness having a first end 110 and a second end 112, suitable for modular insertion 114 within the subchondral bone 20. At least one of the plurality of vertical struts first end 110 and second end 112 is tapered to assist in progressively dissipating stress. The plurality of vertical struts 108 further include a porous, bearing surface 116 contoured to fit the subchondral bone 20 being treated. The porous, bearing surface 116 is configured to include a primary bearing flare 118 of various configurations (FIG. 14B). The primary bearing flare 118 prevents subsidence of the joint support and subchondral support system 106.

Figure 15:
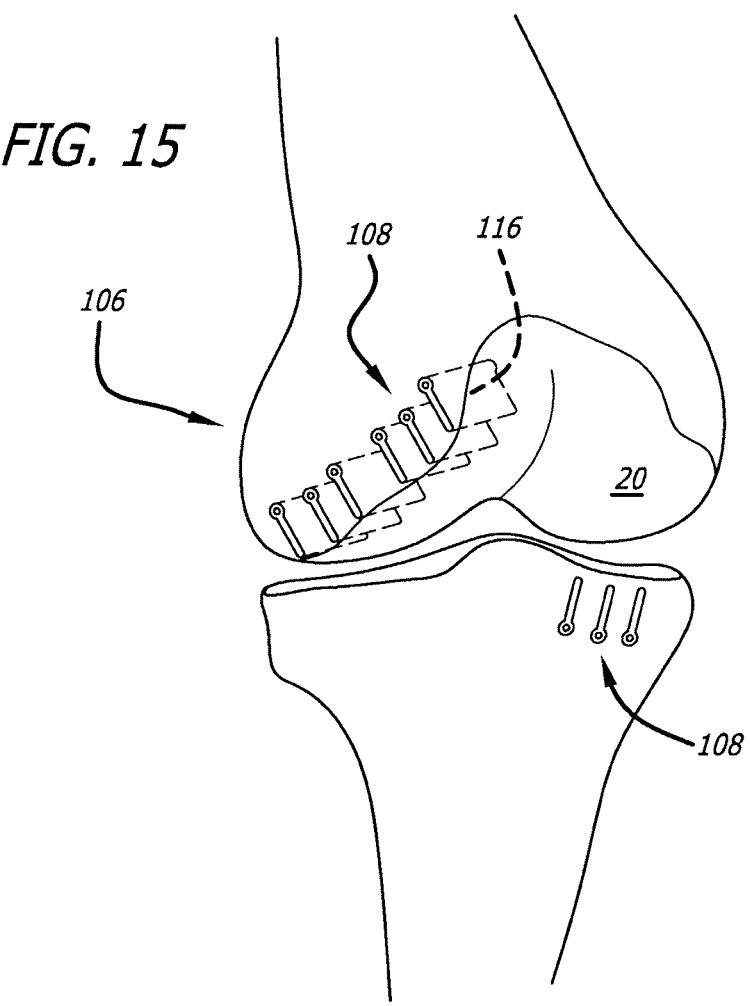
FIG. 15 illustrates the placement of the device of FIG. 14A in subchondral bone of a knee joint in a parallel orientation.

FIG. 15 illustrates the joint support and subchondral support system 106 in subchondral bone 20 of the femoral condyle and tibial plateau in accordance with the present invention.

Figure 16A:
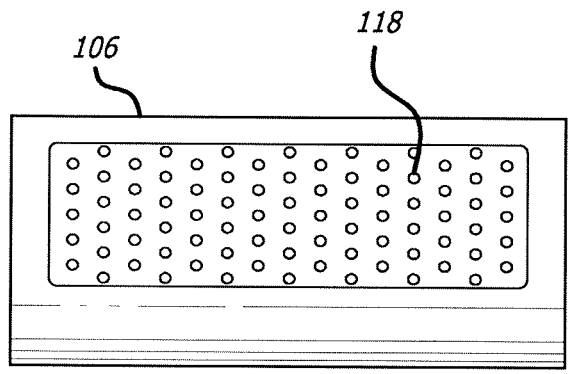
FIGS. 16A-16C illustrate the various degrees of porosity of the device of FIG. 14A.
Figure 16B:
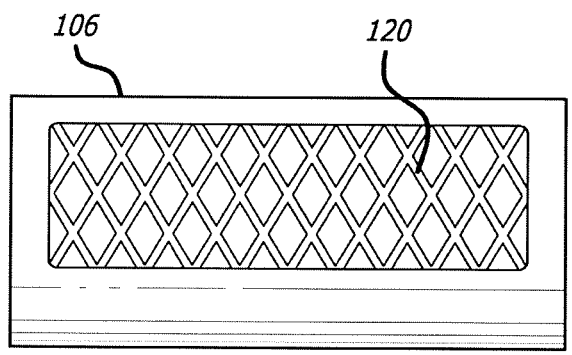
Figure 16C:
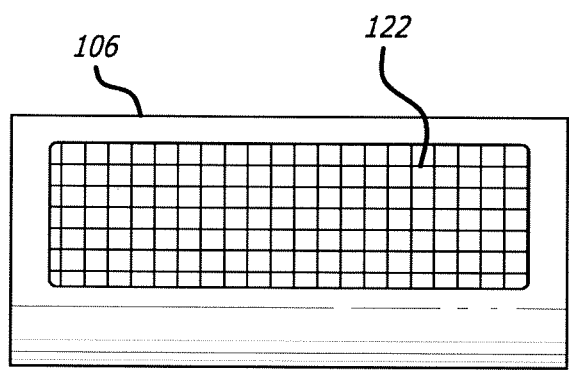

As shown in FIGS. 16A-16C, the device 106 may have a porosity comprised of micropores 118, scaffold-like pores 120, or fibrous matrix material 122. The porosity of the device 106 is within a range of from about 50 microns to about 20 mm.

FIGS. 17A-17G illustrate an enlarged perspective view of the different cross-sectional shapes of the strut device 108, such as a triangular (both polarities) (FIG. 17A), smooth thermometer-like (FIG. 17B), trapezoid (FIG. 17C), flared diamond-shaped (FIG. 17D), oval (FIG. 17E), complex (tapered with flared-diamond) (FIG. 17F), and rectangular (FIG. 17G).

Figure 18:
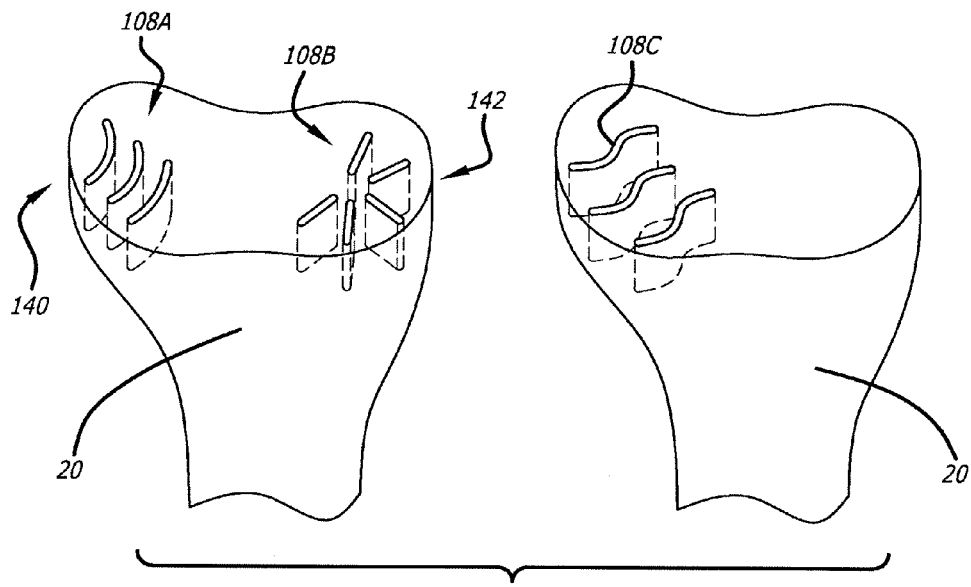
FIG. 18 illustrates the placement of the device of FIG. 14A in subchondral bone of a knee joint in a radial versus parallel orientation.

The plurality of vertical struts 108 can be inserted in either a parallel orientation 140 (FIGS. 15 and 18) or a radial orientation 142 (FIG. 18) within the subchondral bone 20. Radial orientation may enable centripetal load dissipation within the subchondral bone. The top-down geometry of the struts may be curved 108A, straight 108B, or sinusoidal 108C as shown in FIG. 18.

Figure 19:
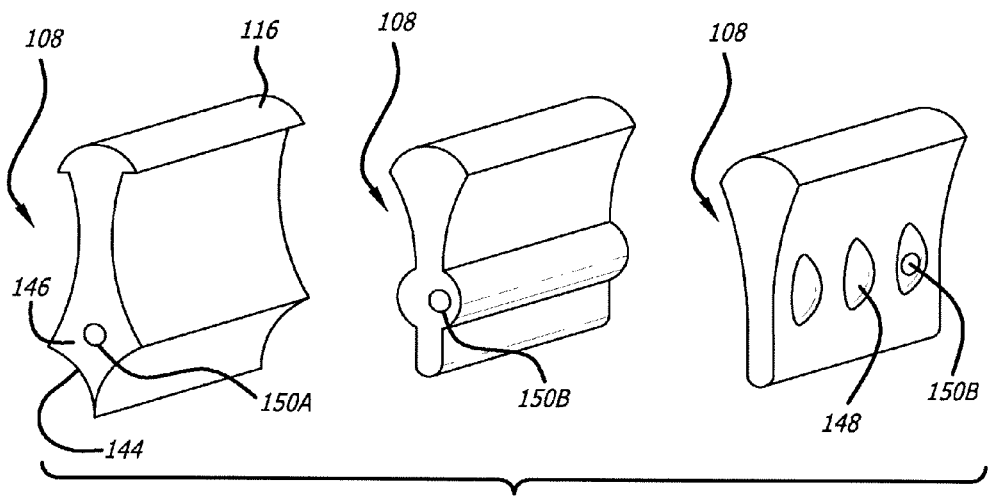
FIG. 19 is an enlarged perspective view of the porous, bearing surface of the embodiment of FIG. 14A with associated secondary flares.

The embodiment of FIG. 19 illustrates an enlarged perspective view of the porous, bearing surface 116 having a secondary bearing flare 144 extending below the bearing surface 116. The secondary bearing flare 144 distributes the load horizontally, along the vertical length of the plurality of vertical struts 108. The secondary bearing flare 144 can be in the form of either a horizontal wing strut 146 or dimple 148. The dimple 148 can be asymmetric in shape in which it is wider towards the joint.

It is contemplated by the present invention that the plurality of vertical struts 108 are implanted within the subchondral bone 20 via side slot insertion as shown in FIG. 15.

Referring further to FIG. 19, at least one active or passive dampening element 150 is attached to the plurality of vertical struts 108. The dampening element may be within the main strut body 150A or housed within the secondary bearing flare 150B. A dampening element, such as a piezoelectric device, converts active mechanical energy to heat or electric, thereby dissipating and dampening the shock. The dampening element 150 may also be inherent in the material properties of the device 106, i.e., silicone-injected porous metal matrix.

The joint support and subchondral support system 106 of the present invention may be fabricated from virtually any biocompatible material, including, but not limited to, metals, metal alloys, carbon fibers, foam metals, ceramics, ceramic composites, elastomer composites, elastomer-carbon fiber composites, chambered or fluid-filled materials, metal matrices, injectable gels, injectable composites with fluid and sold matrices, bone or bone-composite or allografts, crystal or hydroxyapatite materials, plastics (i.e., PEEK), polymers, bioabsorbable composites (i.e., TCP/PLLA), or combinations/composites of the above materials. The preferred materials for the system 106 have inherent elastic or shock absorbing properties.

Figure 20A:
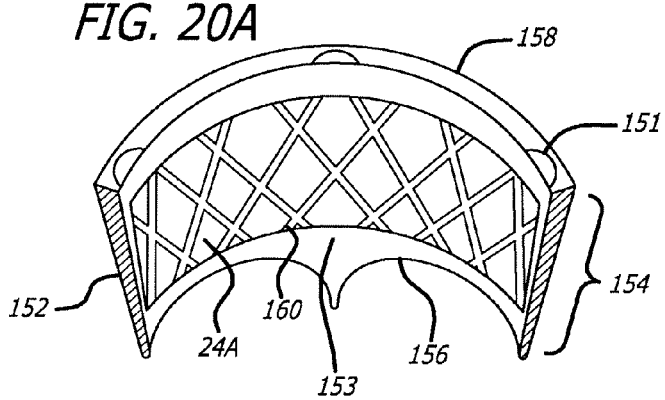
FIG. 20A is a cut-away view of another embodiment of the joint support and subchondral support system according to the present invention.
Figure 20B:
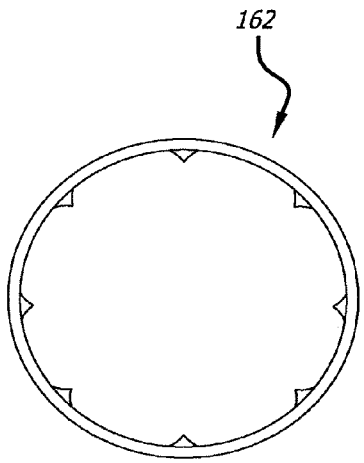
FIG. 20B is a perspective view of the embodiment of FIG. 20A illustrated as a complete circle.
Figure 21A:
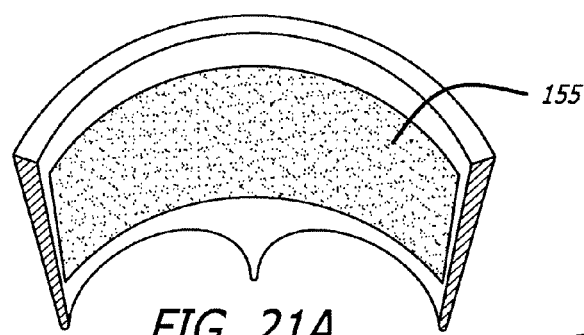
FIGS. 21A-21C illustrate the various degrees of porosity of the device of FIG. 20.
Figure 21B:
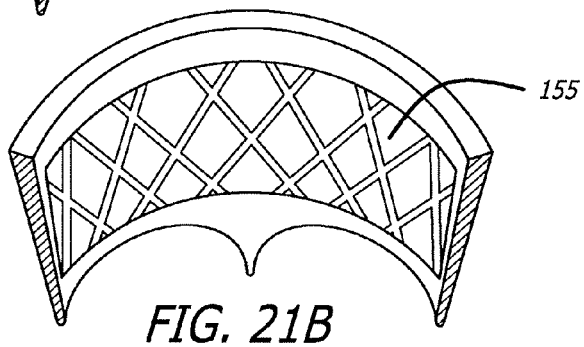
Figure 21C:
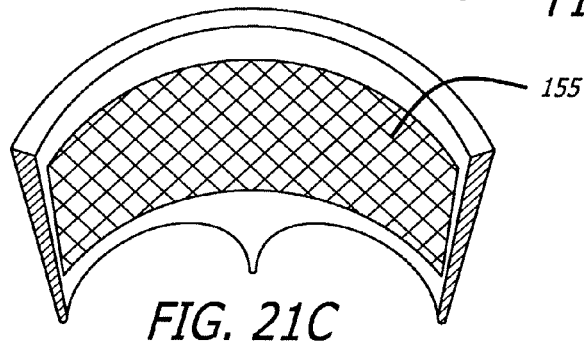

In still a further embodiment of FIG. 20, the joint support and subchondral support system 150 includes at least one non-telescoping primary bearing strut element 152 of variable geometry and thickness having a longitudinal body 154 and a vertically disposed inner edge 156 and outer edge 158, suitable for insertion within the subchondral bone 20. The basic geometric shape 162 of the primary bearing strut element 152 is a circle as illustrated as a cut-away in FIG. 20A and as a complete circle in FIG. 20B. At least one of the plurality of strut elements vertically disposed inner edge 156 and outer edge 158 is tapered. The longitudinal body 154 has a porosity 155 to allow vascularity, bridging bone, and other biologic elements to pass through. The porosity 155 of the primary bearing strut element 152 ranges from about 50 microns to about 20 mm. As shown in FIGS. 21A-21C, the porosity 155 may be comprised of micropores, scaffold-like pores, or a fibrous matrix material, respectively.

Figure 22B:
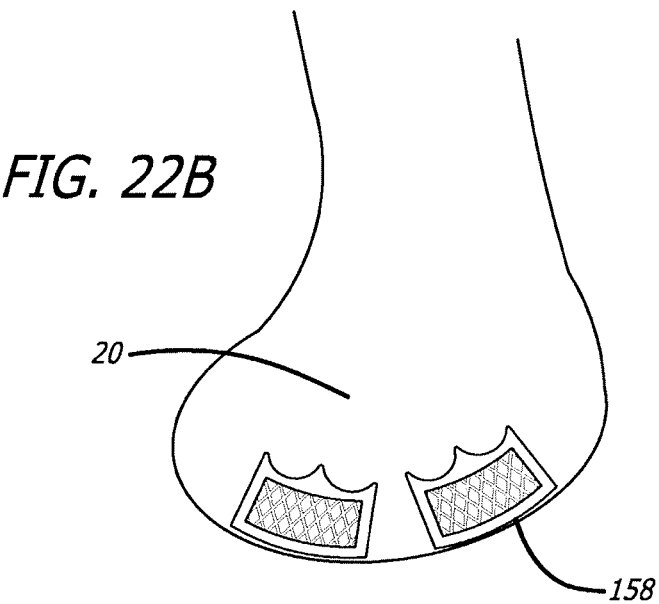
FIGS. 22A-22B illustrate the outer edge of the device of FIG. 20 having concave and convex curvatures.
Figure 22A:
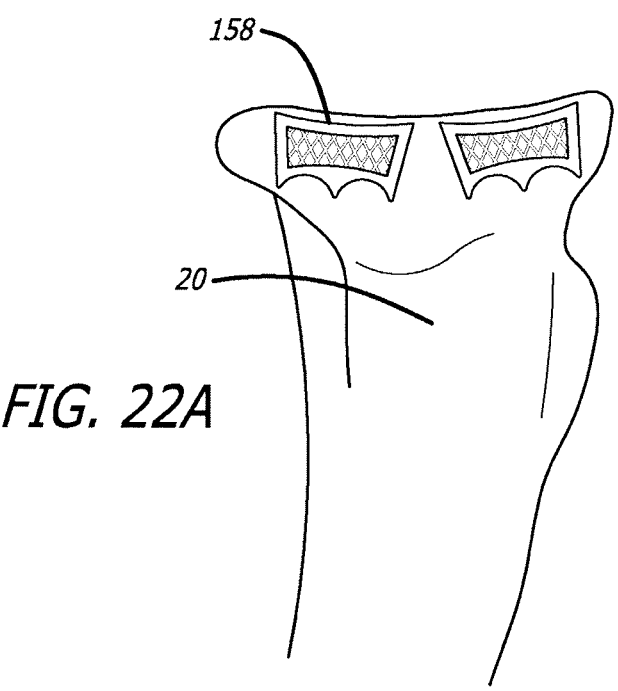
Figure 22C:
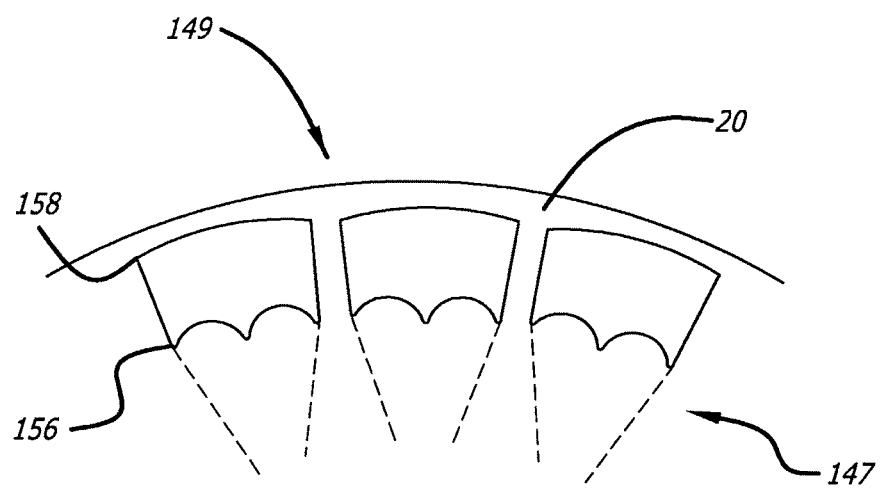
FIG. 22C illustrates the concentric taper of the primary bearing strut element of the embodiment of FIG. 20.
Figure 25A:
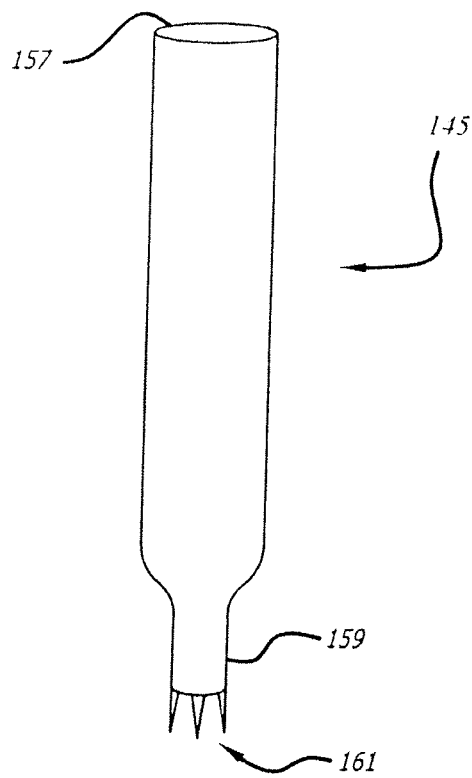
FIG. 25A is an enlarged perspective view of an insertion holder used in conjunction with the embodiment of FIG. 20 during insertion of the device within the subchondral bone.
Figure 25B:
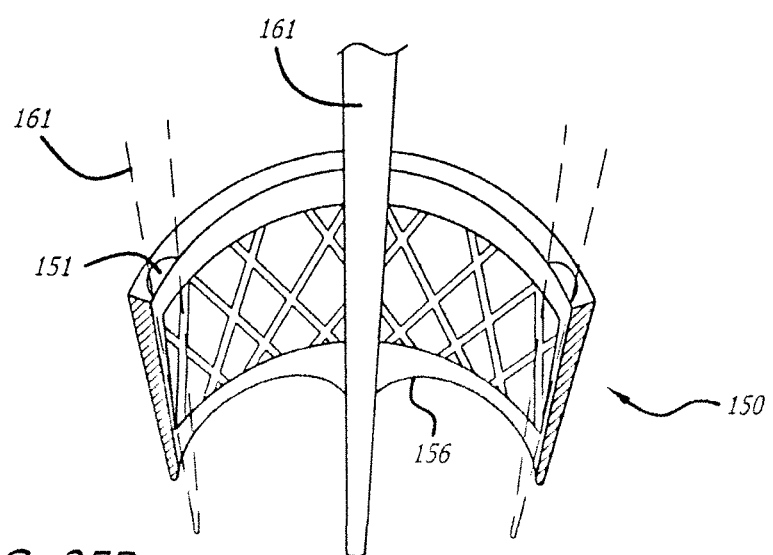
FIG. 25B illustrates the placement of the insertion holder prongs within each of the grooves of the embodiment of FIG. 20 during insertion of the device within the subchondral bone.

The vertically disposed outer edge 158 of the at least one non-telescoping primary bearing strut element 152 is contoured to fit the subchondral bone 20 at the treatment site. As shown in FIGS. 22A-22B, the outer edge 158 may be concave (FIG. 22A) such as the tibial plateau, convex (FIG. 22B) such as the femoral condyle, or complex (not shown) with both concave and convex curvatures, such as the femoral trochlea. The vertically disposed inner edge 156 includes scalloping for penetration of the subchondral bone 20 during insertion of the system 150. The outer edge 158 has a plurality of hollow grooves 151 (FIG. 20) formed vertically therethrough in which the plurality of hollow grooves are configured to receive a multi-pronged longitudinal insertion holder 145 during insertion of the at least one non-telescoping primary bearing strut element 152 within the subchondral bone 20 (FIGS. 25A-25B). In addition to the thickness taper that exists between the outer edge 158 and inner edge 156, a concentric taper 147 of the entire circle is present from the outer edge 158 to the inner edge 156 (FIG. 22C). This allows for subjacent placement in a convex surface 149 as well as further preventing subsidence. The degree of this taper 147 may range from 3-10 degrees.

Figure 23:
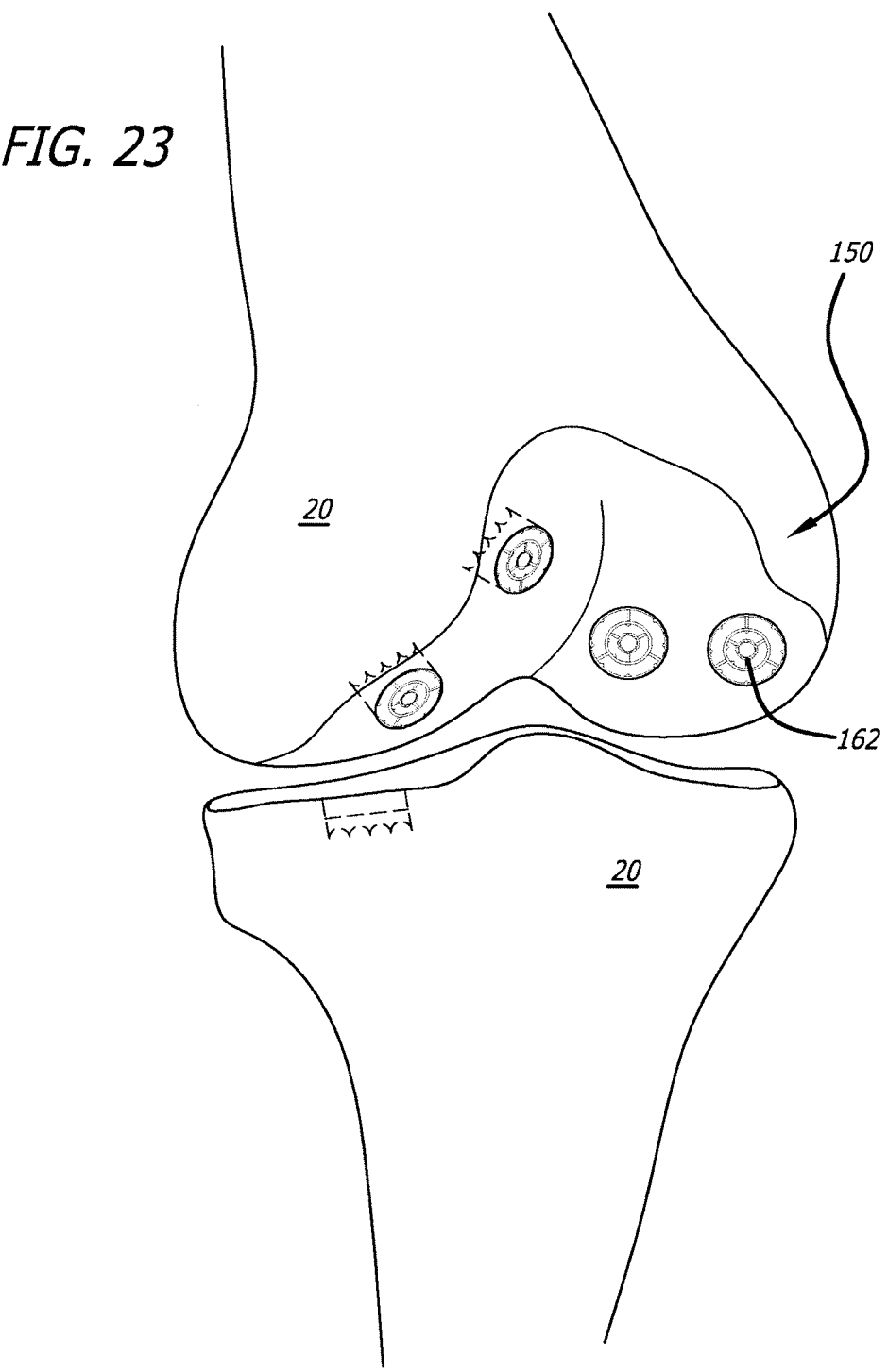
FIG. 23 illustrates the placement of the device of FIG. 20 in subchondral bone of a knee joint by monobloc via antegrade insertion.
Figure 24A:
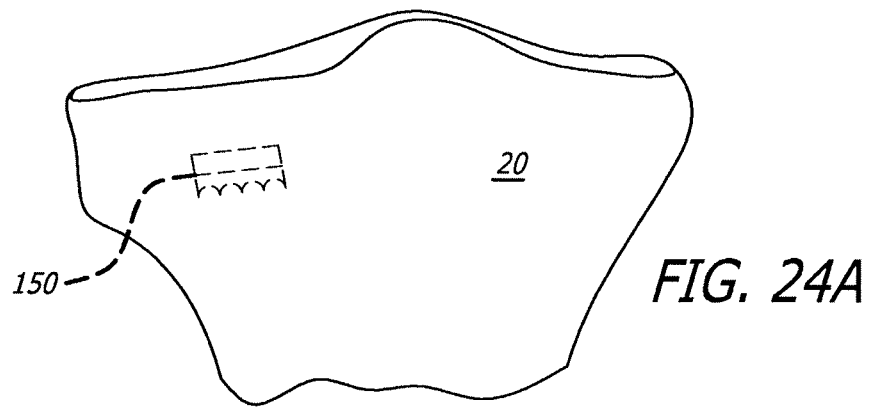
FIGS. 24A-24C illustrate the varying levels of the depth of penetration of the device of FIG. 20.
Figure 24B:
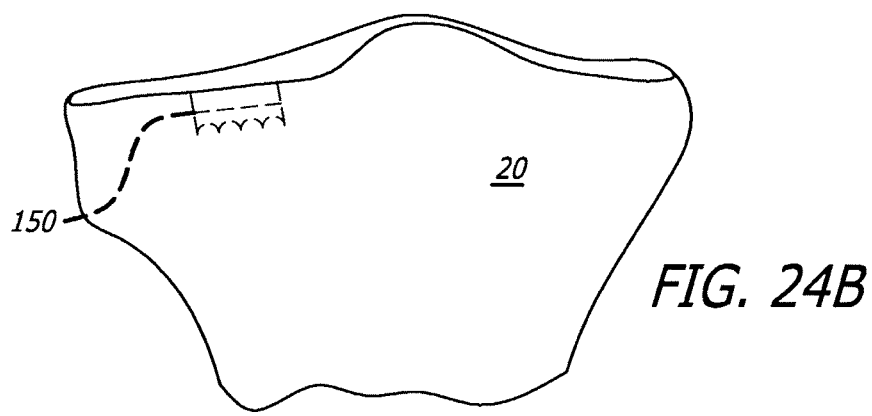
Figure 24C:
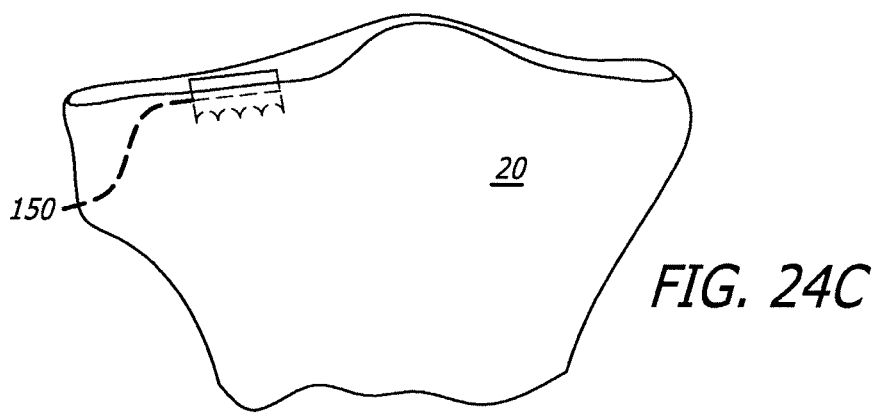

FIG. 23 illustrates the placement of the joint support and subchondral support system 150 in the subchondral bone 20 of the femoral condyle and tibial plateau in accordance with the present invention. The depth of penetration of the device 150 may vary depending on the exact pathology being treated as seen in FIGS. 24A-24C such that it may be below the level of the subchondral plateau (FIG. 24A), at the level of the subchondral plateau (FIG. 24B), or above the subchondral plateau, flush with the native cartilage (FIG. 24C).

FIG. 25A is an enlarged perspective view of a multi-pronged longitudinal insertion holder 145 used in conjunction with the embodiment of FIG. 20 during insertion of the joint support and subchondral support system or device 150 within the subchondral bone 20. The insertion holder 145 has a proximal end 157 and distal end 159. A plurality of prongs or spikes 161 at the distal end 159 are configured to fit in a plurality of hollow grooves or vascular channels 151 at the outer edge 158 of the longitudinal body 154 to effectively hold the device 150 during its insertion within the subchondral bone 20. It is contemplated by the present invention that one insertion holder 145 may be used per device 150.

FIG. 25B illustrates the placement of the insertion holder prongs or spikes 161 within each of the plurality of hollow grooves or vascular channels 151 of the embodiment of FIG. 20 during insertion of the device 150 within the subchondral bone 20. During insertion of the device 150, the plurality of prongs or spikes 161 at the insertion holder distal end 159 are pushed downward in the plurality of hollow grooves or vascular channels 151 and are preferably extended past the inner edge 156. The plurality of prongs or spikes 161 from the inserter holder 145 exit at the scalloped inner edge 156 and outer edge 158 and are pushed deeper into the subchondral bone 20. The device 150 and insertion holder 145 are then tamped into the subchondral bone 20 and the insertion holder 145 is then removed (not shown). The multi-pronged longitudinal insertion holder 145 forms a plurality of vascular channels in the subchondral bone 20 whereby blood/marrow may access the outer edge 158 of the primary bearing strut element 152 via the plurality of hollow grooves or vascular channels 151. Grooves 151 may also be in the form of holes within the primary bearing strut element 152.

Figure 26:
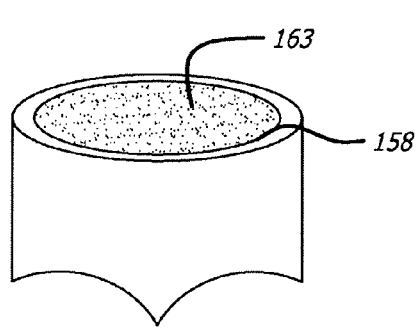
FIG. 26 illustrates a perspective view of the bearing surface cover in accordance with the embodiment of FIG. 20.

As shown in FIG. 26, it is further contemplated by the present invention that a bearing surface cover 163 may be attached to the periphery of the outer edge 158 that serves to contain marrow contents entering via the vascular channels or exogenous substances, injected through the cover (i.e., cultured chondrocytes). This cover 163 is made of either a thin netted or woven material or biologic/synthetic membrane.

Figure 27A:
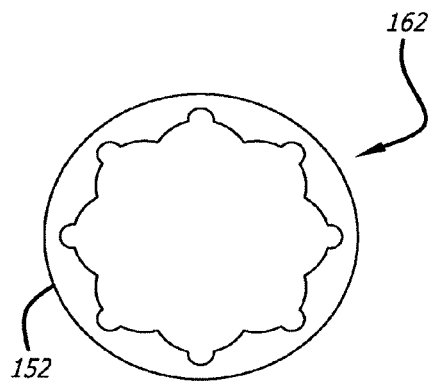
FIGS. 27A-27F illustrate the various geometric shapes that can be formed by the primary bearing strut elements of the embodiment of FIG. 20.
Figure 27B:
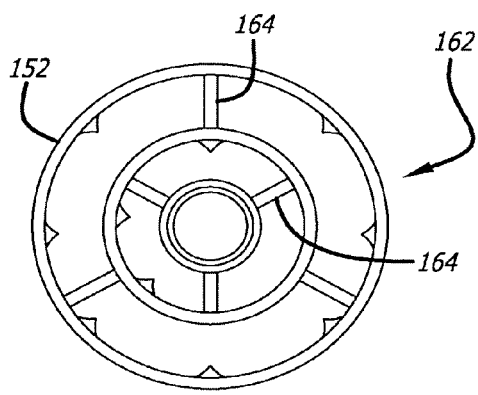
Figure 27C:
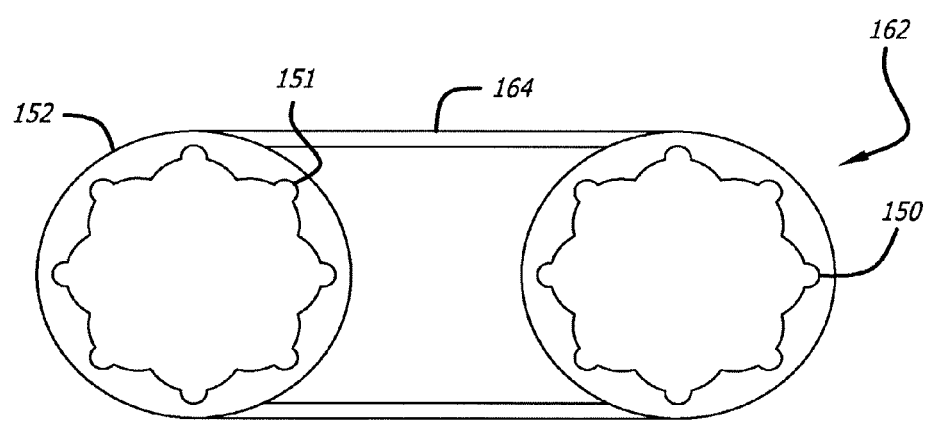
Figure 27D:
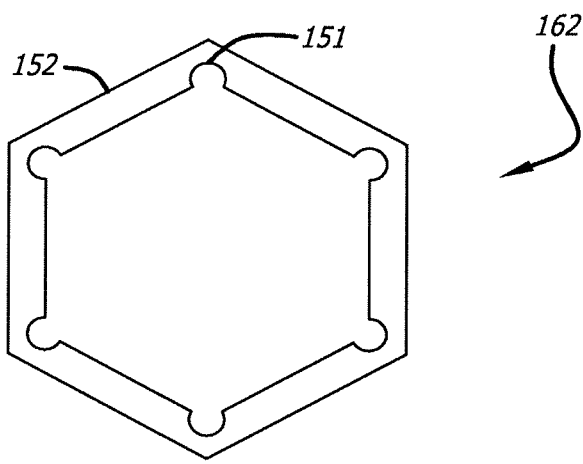
Figure 27E:
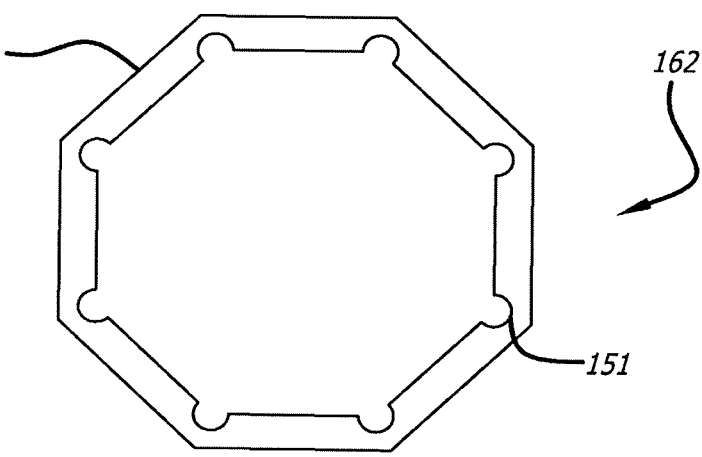
Figure 27F:
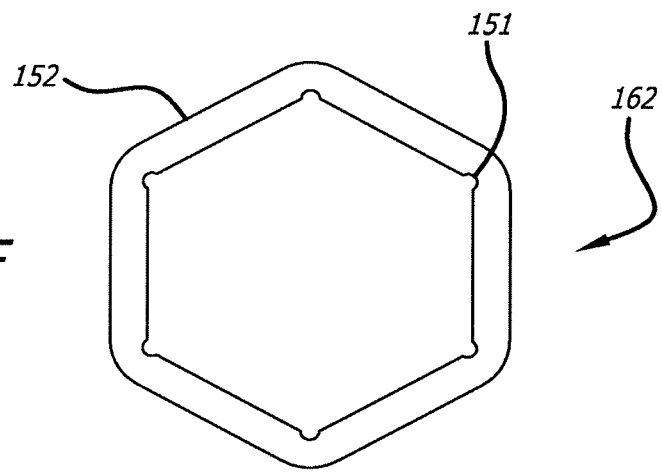

As shown in FIGS. 27A-27F, the geometric shape 162 of the primary bearing strut elements 152 can be a circle (FIG. 27A), multiple concentric circle (FIG. 27B), joined circles (FIG. 27C), hexagon (FIG. 27D), or octagon (FIG. 27E) or other non-linear, non-euclidean shapes, such as a hexagon with smoothed edges (FIG. 27F). The primary bearing strut elements 152 configured to be joined together include at least three connecting struts 164 to form a multiple concentric circle (FIG. 27B) in which each circle 166 of joined together primary bearing strut elements 152 is connected to an adjacent circle 166 by the connecting struts 164.

Figure 28:
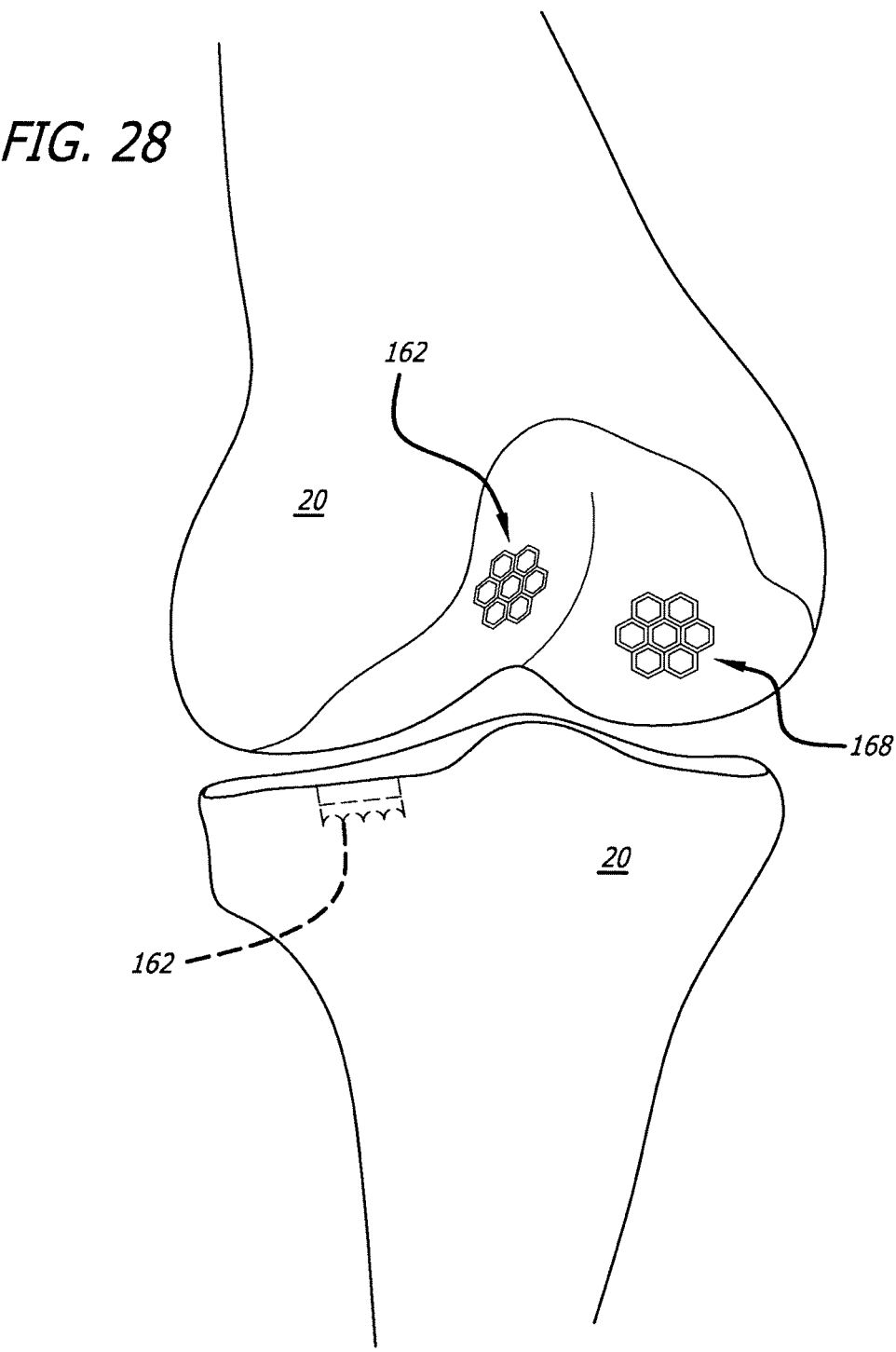
FIG. 28 illustrates the placement of the device of FIG. 18 in subchondral bone of a knee joint with multiple devices joined to each other to form various patterns.

It is further contemplated by the present invention that single or multiple geometric shapes 162 may be configured to be joined to each other in various patterns 168 (i.e., a honeycomb configuration) (FIG. 28) such that the geometric shapes 162 may penetrate the subchondral bone 20 and enable use with different size cartilage lesions at the treatment site. The geometric shapes 162 may mirror the entire joint compartment if the entire compartment is involved, i.e., trochlea, lateral patellar facet, medial tibial platea, etc. The geometric shapes 162 may be inserted within the subchondral bone 20 either piecemeal or monobloc via antegrade insertion (i.e., from the joint surface).

The dimensions of the joint support and subchondral support system 150 generally depend on the size of the lesion being treated. In particular, the primary bearing strut elements 152 configured to be joined together in a geometric shape 162 each have a diameter of from about 1 mm to about 5 cm and a height/depth of from about 1 mm to about 3 cm.

Figure 29A:
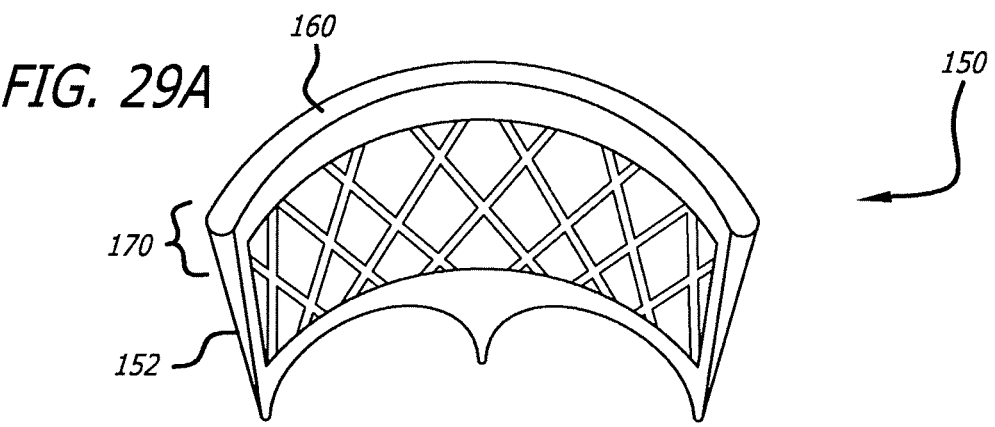
FIG. 29A is a cut-away view of the embodiment of FIG. 20 with a primary bearing flare.
Figure 29B:
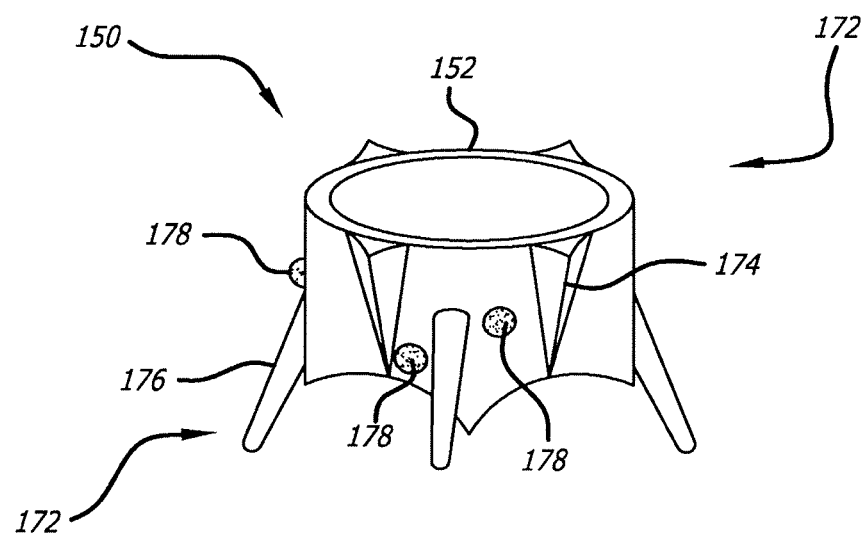
FIG. 29B is a perspective view of the embodiment of FIG. 20 with a secondary flare.

FIG. 29A illustrates a cut-away view of the primary bearing strut element 152 with a primary bearing flare 170. In a further embodiment shown in FIG. 29B, the primary bearing strut element 152 includes a secondary bearing flare 172 extending below the strut element 152. The secondary bearing flare 172 can be in the form of either a vertical double tapered wing strut 174 or obliquely extending arm 176. These secondary flares 172 serve to further resist subsidence.

At least one active or passive dampening element 178 (FIG. 29B) is attached to the primary bearing strut element 152. The dampening element may be inherent to the material properties of the device 150, i.e., silicone-inject porous metal matrix. A dampening element, such as a piezoelectric device, converts active mechanical energy to heat or electric, thereby dissipating and dampening the shock.

The joint support and subchondral support system 150 of the present invention may be fabricated from virtually any biocompatible material, including, but not limited to, metals, metal alloys, carbon fibers, foam metals, ceramics, ceramic composites, elastomer composites, elastomer-carbon fiber composites, chambered or fluid-filled materials, metal matrices, injectable gels, injectable composites with fluid and sold matrices, bone or bone-composite or allografts, crystal or hydroxyapatite materials, plastics (i.e., PEEK), polymers, bioabsorbable composites (i.e., TCP/PLLA), or combinations/composites of the above materials. The preferred materials for the system 150 have inherent elastic or shock absorbing properties.

The methods of use of the joint support and subchondral support system 150 for providing structural and dampening support to damaged subchondral bone adjacent to a body joint are in accordance with the insertion techniques previously discussed above and as shown in the accompanying drawings, namely, FIGS. 20-29, for this embodiment.

Figure 30:
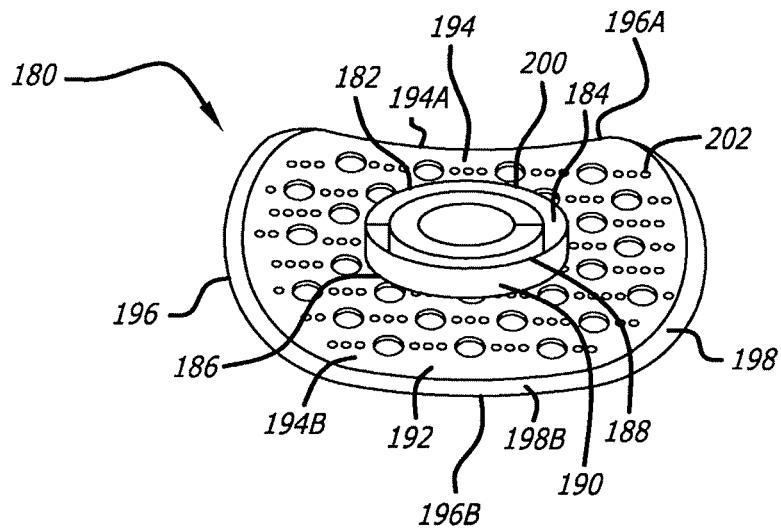
FIG. 30 is a perspective view of a further embodiment of the joint support and subchondral system according to the present invention.

Referring now to FIG. 30 in a further embodiment of the present invention, the joint support and subchondral support system 180 includes a primary bearing strut element 182 of variable geometry and thickness having a longitudinal body 184 and an inner edge 186 and an outer edge 188. The longitudinal body 184 has a porosity to allow vascularity, bridging bone, and other biological elements to pass through. The outer edge 188 has at least two grooves 189 formed therein an inner surface 190 of the longitudinal body 184 and contoured to fit the subchondral bone 20 at the treatment site. The system 180 further includes a contoured, porous plate 192 having a variable shaped inner surface 194, outer surface 196, and peripheral surface 198 of variable thickness extending between the inner surface 194 and outer surface 196, suitable for insertion within the subchondral bone 20. The inner surface 194, outer surface 196, and peripheral surface 198 each have a respective concave portion 194A, 196A, 198A and a respective convex portion 194B, 196B, 198B. The inner edge 186 of the primary bearing strut element 182 is in direct communication with the contoured, porous plate 192 within the subchondral bone being treated. The contoured, porous plate 192 of the joint support and subchondral support system 180 may include a plurality of surface dimples 202 and undersurface pimples 204 as previously described above.

Figure 31:
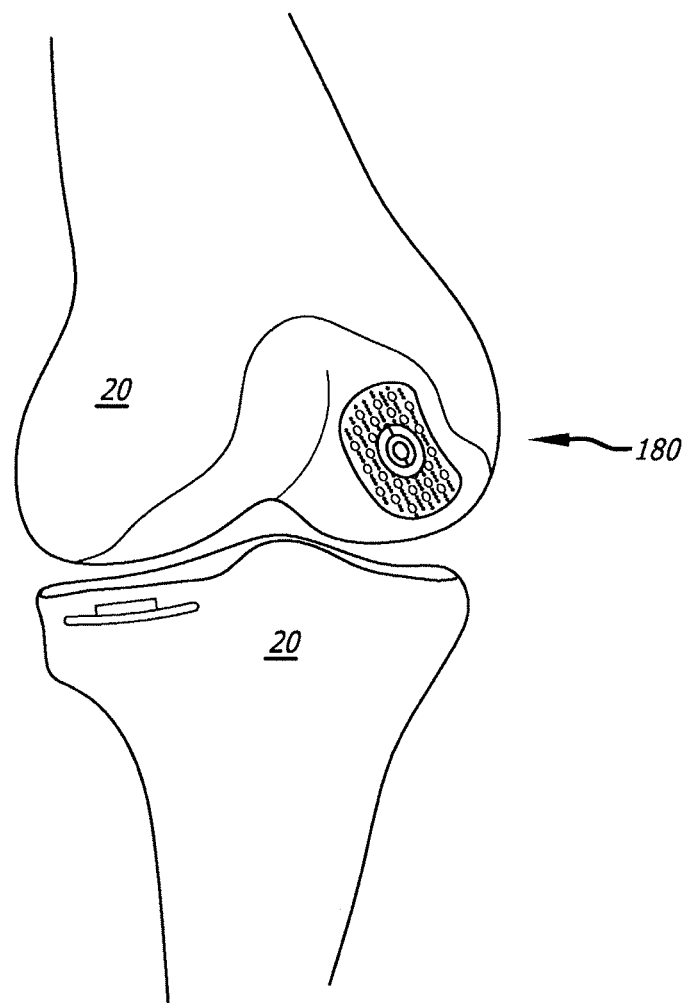
FIG. 31 illustrates the placement of the device of FIG. 30 in subchondral bone of a knee joint.

FIG. 31 illustrates the placement of the joint support and subchondral support system 180 in the subchondral bone 20 of the femoral condyle and tibial plateau in accordance with the present invention.

It is contemplated by the present invention that the joint support and subchondral support system 180 may be inserted within the subchondral bone 20 according to the insertion techniques previously discussed above.

At least one active or passive dampening element 206 is attached to the joint support and subchondral support system 180. A dampening element, such as a piezoelectric device, converts active mechanical energy to heat or electric, thereby dissipating and dampening the shock.

As with the previous embodiments, the joint support and subchondral support system 180 of the present invention may be fabricated from virtually any biocompatible material, including, but not limited to, metals, metal alloys, carbon fibers, foam metals, ceramics, ceramic composites, elastomer composites, elastomer-carbon fiber composites, chambered or fluid-filled materials, metal matrices, injectable gels, injectable composites with fluid and sold matrices, bone or bone-composite or allografts, crystal or hydroxyapatite materials, plastics (i.e., PEEK), polymers, bioabsorbable composites (i.e., TCP/PLLA), or combinations/composites of the above materials. The preferred materials for the system 180 have inherent elastic or shock absorbing properties.

Figure 32:
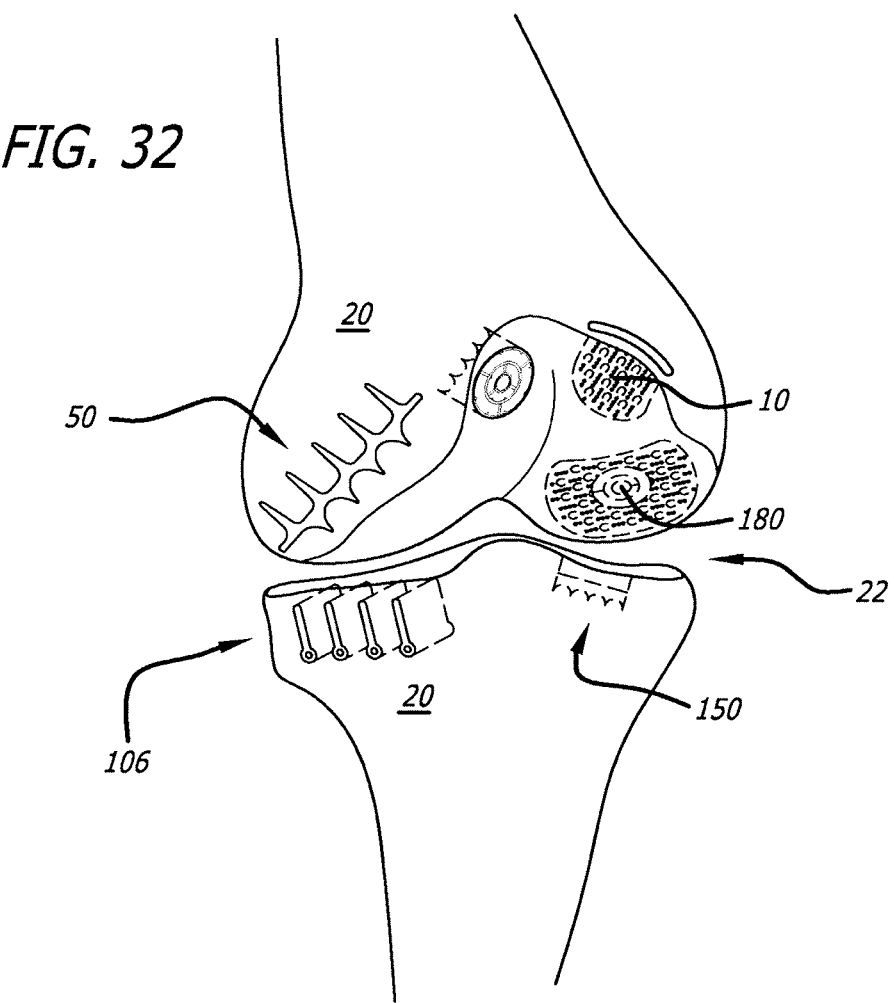
FIG. 32 is a perspective view of the placement of the joint support and subchondral support system of each of the embodiments in subchondral bone of a knee joint.

FIG. 32 illustrates the placement of the joint support and subchondral support system 10, 50, 106, 150, 180 of each of the aforementioned embodiments discussed above in subchondral bone 20 of a knee joint 22. The present invention contemplates that each of the embodiments of the joint support and subchondral support system 10, 50, 106, 150, 180 may be used in combination with one another to provide enhanced structural and dampening support to damaged subchondral bone 20 adjacent to a body joint.

The above-described elements for each of the embodiments may be varied in design, function, operation, configuration, materials, and dimensions, and are not limited to the descriptions provided herein.

Having now described the invention in accordance with the requirements of the patent statutes, those skilled in the art will understand how to make changes and modifications in the present invention to meet their specific requirements or conditions. Such changes and modifications may be made without departing from the scope and spirit of the invention as set forth in the following claims.

What is claimed is:

1. A joint support and subchondral support system for providing structural support to damaged subchondral bone adjacent to a body joint, comprising:

at least one non-telescoping, single walled primary bearing strut element of variable geometry and thickness having a longitudinal body with open opposing ends and a vertically disposed inner edge and a vertically disposed outer edge, suitable for insertion within the subchondral bone, wherein the at least one non-telescoping single walled primary bearing strut element includes a concentric taper from the outer edge to the inner edge;

the longitudinal body having a porosity to allow vascularity, bridging bone, and other biological elements to pass through to promote healing at a treatment site;

the vertically disposed inner edge having pronged scalloping to first penetrate the subchondral bone during insertion and to maintain the at least one non-telescoping, single walled primary bearing strut element in place within the subchondral bone; and the vertically disposed outer edge having a plurality of hollow grooves formed vertically therethrough, wherein the plurality of hollow grooves are configured to receive a multi-pronged longitudinal insertion holder during insertion of the at least one non-telescoping single walled primary bearing strut element within the subchondral bone, and the vertically disposed outer edge is contoured to fit the subchondral bone at the treatment site.

2. The joint support and subchrondral support system of claim 1, wherein the multi-pronged longitudinal insertion holder forms a plurality of vascular channels in the subchondral bone during insertion of the at least one non-telescoping, single walled-primary bearing strut element within the subchondral bone whereby blood or marrow may access the vertically disposed outer edge through the plurality of hollow grooves or vascular channels.

3. The joint support and subchondral support system of claim 1, wherein single or multiple geometric shapes of the at least one non-telescoping single walled primary bearing strut element may be configured to be joined to each other in various patterns such that the single or multiple geometric shapes penetrate the subchondral bone at the treatment site.

4. The joint support and subchondral support system of claim 3, wherein the single or multiple geometric shapes configured to be joined together include at least three connecting struts to form a multiple concentric circle in which each circle of the at least one non-telescoping, single walled primary bearing strut element is connected to an adjacent circle by the connecting struts.

5. The joint support and subchondral support system of claim 1, wherein the at least one non-telescoping, single walled primary bearing strut element has a diameter of from about 1 mm to about 5 cm and a height/depth of from about 1 mm to about 3 cm.

6. The joint support and subchondral support system of claim 1, wherein the at least one non-telescoping, single walled primary bearing strut element includes a primary bearing flare for resisting subsidence within the subchondral bone at the treatment site.

7. The joint support and subchondral support system of claim 1, wherein the at least one non-telescoping, single walled primary bearing strut element includes a secondary flare extending below the strut element for further resisting subsidence within the subchondral bone at the treatment site.

8. The joint support and subchondral support system of claim 7, wherein the secondary flare is at least one of a vertical, double-tapered wing strut, and obliquely extending arm.

9. The joint support and subchondral support system of claim 1, wherein the porosity of the longitudinal body may be comprised of micropores, scaffold-like pores, or a fibrous matrix material.

10. The joint support and subchondral support system of claim 1, wherein a biocompatible bearing surface cover may be attached to a periphery of the vertically disposed outer edge to contain marrow contents entering through vascular channels or exogenous substances injected through the cover.

11. A joint support and subchondral support system for providing dampening support to damaged subchondral bone adjacent to a body joint, comprising:
at least one non-telescoping, primary bearing strut element of variable geometry and thickness; and
at least one active or passive dampening element suitable for attachment to the at least one non-telescoping, primary bearing strut element for dissipating and dampening shock within the subchondral bone; the at least one non-telescoping, primary bearing strut element having a longitudinal body with open opposing ends and a vertically disposed inner edge and a vertically disposed outer edge, suitable for insertion within the subchondral bone, wherein the at least one non-telescoping primary bearing strut element includes a concentric taper from the outer edge to the inner edge;
the longitudinal body having a porosity to allow vascularity, bridging bone, and other biological elements to pass through to promote healing at a treatment site;
the vertically disposed inner edge having pronged scalloping to first penetrate the subchondral bone during insertion and to maintain the at least one non-telescoping, primary bearing strut element in place within the subchondral bone; and
the vertically disposed outer edge having a plurality of hollow grooves formed vertically therethrough, wherein the plurality of hollow grooves are configured to receive a multi-pronged longitudinal insertion holder during insertion of the at least one non-telescoping primary bearing strut element within the subchondral bone, and the vertically disposed outer edge is contoured to fit the subchondral bone at the treatment site.

12. The joint support and subchondral support system of claim 11, wherein the at least one non-telescoping primary bearing strut element may have a geometry in the form of a multiple concentric circle, joined circles, hexagon, octagon, or other non-euclidean shapes.

\* \* \* \* \*